US012698313B2

(12) United States Patent
Chung et al.

(10) Patent No.: US 12,698,313 B2
(45) Date of Patent: Aug. 4, 2026

(54) BONE MORPHOGENETIC PROTEIN-9 AND -10 VARIANTS WITH ENHANCED THERAPEUTIC EFFECT DUE TO REDUCED SIDE EFFECTS OF ECTOPIC OSSIFICATION AND PHARMACEUTICAL COMPOSITION COMPRISING SAME

(71) Applicant: NIBEC CO., LTD., Chungcheongbuk-do (KR)

(72) Inventors: Chong-Pyoung Chung, Seoul (KR); Yoon Jeong Park, Seoul (KR); Jue-Yeon Lee, Gyeonggi-do (KR); Gook-Jin Yoon, Seoul (KR); Dong Woo Lee, Seoul (KR)

(73) Assignee: NIBEC CO., LTD., Chungcheongbuk-Do (KR)

( * ) Notice: Subject to any disclaimer, the term of this patent is extended or adjusted under 35 U.S.C. 154(b) by 679 days.

(21) Appl. No.: 18/040,643

(22) PCT Filed: Aug. 12, 2021

(86) PCT No.: PCT/KR2021/010744
§ 371 (c)(1),
(2) Date: Feb. 4, 2023

(87) PCT Pub. No.: WO2022/035260
PCT Pub. Date: Feb. 17, 2022

(65) Prior Publication Data
US 2023/0272025 A1 Aug. 31, 2023

(30) Foreign Application Priority Data
Aug. 13, 2020 (KR) ........................ 10-2020-0101759

(51) Int. Cl.
| | |
|---|---|
| *C07K 16/46* | (2006.01) |
| *A61K 39/00* | (2006.01) |
| *A61K 47/68* | (2017.01) |
| *C07K 14/51* | (2006.01) |
| *C07K 19/00* | (2006.01) |

(52) U.S. Cl.
CPC .......... *C07K 14/51* (2013.01); *A61K 47/6811* (2017.08); *C07K 2319/30* (2013.01)

(58) Field of Classification Search
None
See application file for complete search history.

(56) References Cited

U.S. PATENT DOCUMENTS

| | | | | |
|---|---|---|---|---|
| 7,459,527 | B2 * | 12/2008 | Desjarlais | A61P 19/08 435/69.1 |
| 7,910,101 | B2 | 3/2011 | Cunningham et al. | |
| 2009/0017019 | A1 * | 1/2009 | Shields | A61P 3/10 435/375 |
| 2013/0281371 | A1 | 10/2013 | Kumar et al. | |
| 2017/0209540 | A1 | 7/2017 | Morrell et al. | |

FOREIGN PATENT DOCUMENTS

| | | |
|---|---|---|
| CN | 107760779 A | 3/2018 |
| JP | 2018070625 A | 5/2018 |
| KR | 10-2017-0029576 A | 3/2017 |
| WO | 2010065439 A1 | 6/2010 |
| WO | 2010126169 A1 | 11/2010 |
| WO | 2012010553 A1 | 1/2012 |
| WO | 2012066075 A1 | 5/2012 |
| WO | 2012170438 A2 | 12/2012 |
| WO | 2013188181 A1 | 12/2013 |
| WO | WO-2018144968 A1 * 8/2018 ............. C07K 14/51 |

OTHER PUBLICATIONS

Potez et al. Characterization of a B16-F10 melanoma model locally implanted into the ear pinnae of C57BL/6 mice. PLOS ONE 13( 11): e0206693, 19 pages; (Nov. 5, 2018). (Year: 2018).*

Morel. Mouse models of human autoimmune diseases: Essential tools that require proper controls, Plos Biology vol. 2/No. 8:1061-1064, (Aug. 2004). (Year: 2004).*

Justice et al. Using the mouse to model human disease: increasing validity and reproducibility, Disease, Models & Mechanisms 9: 101-103, (2016). (Year: 2016).*

Search Report issued on Jul. 17, 2024 for European Patent Application 21856266.8.

Hassanisaber, L.R., et al., "Effect of BMP-9on endothelial cells and its role in atheroslerosis", Frontiers in Bioscience, Landmark, 2019, pp. 994-1023, vol. 24.

Kharitonenkov, T., et al., "FGF-21 as a novel metabolic regulator", The Journal of Clinical Investigation, 2005, pp. 1627-1635, vol. 115, No. 6, http://www.jci.org.

Search Report issued on Jul. 28, 2025 for European Patent Application 25169364.4.

Jung, J.W., et al., "Bone morphogenetic protein-9 is a potent growth inhibitor of hepatocellular carcinoma and reduces the liver cancer stem cells", Oncotarget, 2016, pp. 73754-73768, vol. 7, No. 45.

Office Action issued on Aug. 13, 2025 for Korean Patent Application 10-2020-0101759.

English Translation of Office Action issued on Aug. 13, 2025 for Korean Patent Application 10-2020-0101759.

(Continued)

*Primary Examiner* — Bridget E Bunner
*Assistant Examiner* — Regina M DeBerry
(74) *Attorney, Agent, or Firm* — HULTQUIST, PLLC; Steven J. Hultquist

(57) ABSTRACT

The present invention relates to a BMP-9 variant and a derivative thereof. The variant stimulates endothelial cell-specific signaling, but does not stimulate ectopic ossification-related signaling, as compared to wild-type BMP-9, and thus has the effects of enhancing therapeutic effects on various diseases, including tumors, cardiovascular disease, fibrotic diseases, inflammatory diseases, metabolic diseases, and autoimmune diseases, and reducing side effects.

10 Claims, 5 Drawing Sheets

Specification includes a Sequence Listing.

(56)     References Cited

OTHER PUBLICATIONS

Salmon, R.M., et al., "Molecular basis of ALK1-mediated signalling by BMP9/BMP10 and their prodomain-bound forms", Nature Communications, 2020, doi.org/10.1038/s41467-020-15425-3, vol. 11, No. 1621.

Wang, C., et al., "Bone morphogenetic protein-2 exhibits therapeutic benefits for osteonecrosis of the femoral head through induction of cartilage and bone cells", Experimental and Therapeutic Medicine, 2018, pp. 4298-4308, vol. 15.

* cited by examiner

Features of pcDNA™ 3.4-TOPO®
6011 nucleotides

| | |
|---|---|
| CMV promoter ($P_{CMV}$): | 47–726 |
| CMV for primer binding site: | 584–604 |
| TOPO® cloning site: | 741 |
| WPRE: | 782–1379 |
| pcDNA™ 3.4 rev primer binding site: | 822–844 (c)* |
| TK polyadenylation signal (TK pA): | 1384–1655 |
| SV40 early promoter ($P_{SV40}$): | 2124–2493 |
| Neomycin resistance gene: | 2529–3323 |
| SV40 polyadenylation site (SV40 pA): | 3499–3629 |
| pUC origin: | 4012–4685 (c) |
| Ampicillin resistance gene: | 4830–5690 (c) |
| bla promoter: | 5691–5789 (c) |

*(c): complementary strand

NT : No treatment
C1 : Negative control
C2 : Wild type BMP9
2, 4, 6 : Variant BMP9 (Point mutated, SEQ ID NOs: 2, 4, 6)

BONE MORPHOGENETIC PROTEIN-9 AND -10 VARIANTS WITH ENHANCED THERAPEUTIC EFFECT DUE TO REDUCED SIDE EFFECTS OF ECTOPIC OSSIFICATION AND PHARMACEUTICAL COMPOSITION COMPRISING SAME

CROSS-REFERENCE TO RELATED APPLICATIONS

This application is a U.S. national phase under 35 USC § 371 of International Patent Application No. PCT/KR2021/010744 filed Aug. 12, 2021, which in turn claims priority under 35 USC § 119 of Korean Patent Application No. 10-2020-0101759 filed Aug. 13, 2020. The disclosures of all such applications are hereby incorporated herein by reference in their respective entireties, for all purposes.

REFERENCE TO SEQUENCE LISTING

This application includes an electronically submitted sequence listing in .txt format. The .txt file contains a sequence listing entitled "664_UpdatedSeqListing_ST25.txt" created on Nov. 30, 2025 and is 117,170 bytes in size. The sequence listing contained in this .txt file is part of the specification and is hereby incorporated by reference herein in its entirety.

TECHNICAL FIELD

The present invention relates to a BMP-9 variant and a derivative thereof, and more particularly to a BMP-9 variant and a derivative thereof, in which side effects of ectopic ossification are reduced and therapeutic effects are enhanced in the treatment of various diseases, disorders and conditions, including tumors, cardiovascular diseases, fibrotic diseases, and metabolic diseases.

BACKGROUND ART

BMP-9 binds to a unique receptor, rather than binding to conventionally known BMP receptors, and is distinguished from other types of BMPs because of diverse roles thereof in a variety of intracellular processes. For example, BMP-9 is produced in the liver and is able to suppress lipid metabolism, control hepatic glucose production, regulate the growth and migration of endothelial cells in the cardiovascular system, and inhibit cardiomyoblast fibrosis. In particular, in the cardiovascular system, together with BMP-10, BMP-9 binds to endothelial ALK-1 receptors, BMPR-II, and endoglin, and is thus involved in vascular homeostasis and blood pressure regulation. In many documents, it has been reported that, when BMP-9 and BMP-10 are applied to pulmonary arterial hypertension or myocardial fibrosis caused by a deletion of the corresponding receptor, the symptoms are alleviated, indicating high utility of BMP-9 as a therapeutic material. Moreover, BMP-9 is one of powerful BMPS that may induce the death of prostate cancer cells depending on the type of tumor and may regulate osteogenic differentiation in bone tissue. In addition, BMP-9 is known to have high potential as a new anti-diabetic or anti-obesity therapeutic target because it is effective at improving insulin sensitivity.

Accordingly, for the development of new therapeutic agents targeting growth factors including BMP-9, attempts have been made to increase the biological activity of growth factors by substituting, introducing, and removing some amino acids of wild-type growth factors to create mutations (WO 2010/065439). However, a problem associated with the direct use of growth factors including BMP-9 as biotherapeutic agents is that ectopic ossification and deformity growth factor action are simultaneously expressed. This is due to the complexity of receptors of growth factors including BMP-9, and there are still few cases of alleviating side effects related to ectopic ossification. The receptors of BMP-9 and BMP-10 are mainly present in vascular endothelial cells, and are known to be involved in vascular function regulation while acting as ligands of Alk-1 and BMPR-II. Specifically, BMPR-II forms a complex with ALK-1 and selectively reacts with BMP-9 or BMP-10. As such, in the case in which the receptor is deleted or BMP-9 or BMP-10 is deficient, the most frequent diseases are pulmonary arterial hypertension and myocardial fibrosis. In particular, BMP-9 acts directly on endothelial cells to enhance the integrity of the inner wall of blood vessels, thus increasing vascular stability, thereby inhibiting vascular cell death or angiogenesis. Moreover, unlike other types of BMPs, such as BMP-2, BMP-4, BMP-6, etc., BMP-9 is known to promote endothelial cell activity even at low concentrations that do not cause ossification. However, BMP-9 may also induce ectopic ossification at high concentrations, and as such, the application of variants in which the ectopic ossification n function is controlled is required in actual clinical practice.

In addition, it has been pointed out that the very short in-vivo half-life of the wild type due to the properties of growth factors makes commercialization as a therapeutic agent difficult (Kharitonenkov A. et al., Journal of Clinical Investigation, 115:1627-1635, 2005). BMP-9 has a short in-vivo half-life of 10 minutes to 1 hour in mice and 1.5 hours to 2 hours in monkeys, and if it is developed as a therapeutic agent, it has the disadvantage of having to administer the same daily. To date, various techniques have been reported to increase the in-vivo half-life of recombinant proteins. There is an example in which a protein is linked with polyethylene glycol (PEG), which is a polymer material, so that the molecular weight thereof is increased, thereby inhibiting renal excretion, ultimately increasing the residence time in vivo (WO 2012/066075). Also, there is an example in which the half-life is increased by fusing a fatty acid that binds to human albumin to a growth factor molecule (WO 2012/010553). Furthermore, there is an example of increasing the half-life while exhibiting the same pharmacological activity as the mechanism of action of the growth factor by synthesizing an agonistic antibody that specifically binds to a human growth factor receptor alone or a complex with beta-Klotho (WO 2012/170438). In addition, there is an example in which the half-life is increased by synthesizing a long-acting fusion protein in which Fc of: immunoglobulin IgG is linked to a growth factor molecule (WO 2013/188181).

Accordingly, the present inventors have made great efforts on the study of BMP9-based therapeutic variant proteins to inhibit ectopic ossification and extend the action time, and thus ascertained that some variants may inhibit ectopic ossification and have increased in-vivo half-life, thereby culminating in the present invention.

The information described in this background section is only for improving understanding of the background of the present invention, and is not to be construed as including information forming the related art already known to those of ordinary skill in the art to which the present invention belongs.

PRIOR ART

Patent Literature (Patent Document 1) WO 2010/065439
(Patent Document 2) WO 2012/066075
(Patent Document 3) WO 2012/010553
(Patent Document 4) WO 2012/170438
(Patent Document 5) WO 2013/188181

Non-Patent Literature (Non-Patent Document 1) Kharitonenkov A. et al., Journal of Clinical Investigation, 115:1627-1635, 2005

SUMMARY OF THE INVENTION

It is an object of the present invention to provide a bone morphogenetic protein-9 (BMP-9) variant and a fusion thereof with reduced side effects of ectopic ossification.

It is another object of the present invention to provide various therapeutic bone uses of the morphogenetic protein-9 (BMP-9) variant and the fusion thereof.

It is still another object of the present invention to provide a pharmaceutical composition for preventing or treating tumors, inflammatory diseases, metabolic diseases, or autoimmune diseases, comprising the BMP-9 variant or the fusion thereof.

It is yet another object of the present invention to provide a method of preventing or treating tumors, inflammatory diseases, metabolic diseases, or autoimmune diseases, comprising administering the BMP-9 variant or the fusion thereof.

It is still yet another object of the present invention to provide the use of the BMP-9 variant and the fusion thereof for the prevention or treatment of tumors, inflammatory diseases, metabolic diseases, or autoimmune diseases.

It is even yet another object of the present invention to provide the use of the BMP-9 variant and the fusion thereof for the manufacture of a medicament for the treatment of tumors, inflammatory diseases, metabolic diseases, or autoimmune diseases.

In order to accomplish the above objects, the present invention provides a bone morphogenetic protein-9 (BMP-9) variant represented by any one amino acid sequence selected from the group consisting of SEQ ID NOs: 2 to 29.

In addition, the present t invention provides a BMP-9 variant-Fc fusion protein in which an Fc fragment of an immunoglobulin is linked to the BMP-9 variant.

In addition, the present invention provides a pharmaceutical composition for treating a tumor comprising the BMP-9 variant or the BMP-9 variant-Fc fusion protein as an active ingredient.

In addition, the present invention provides a pharmaceutical composition for treating an inflammatory disease comprising the BMP-9 variant or the BMP-9 variant-Fc fusion protein as an active ingredient.

In addition, the present invention provides a pharmaceutical composition for treating a metabolic disease comprising the BMP-9 variant for the BMP-9 variant-Fc fusion protein as an active ingredient.

In addition, the present invention provides a pharmaceutical composition for treating an autoimmune disease comprising the BMP-9 variant or the BMP-9 variant-Fc fusion protein as an active ingredient.

In addition, the present invention provides a method of preventing or treating a tumor, an inflammatory disease, a metabolic disease, or an autoimmune disease, comprising administering the BMP-9 variant or the BMP-9 variant-Fc fusion protein.

In addition, the present invention provides the use of the BMP-9 variant or the BMP-9 variant-Fc fusion protein for the prevention or treatment of a tumor, an inflammatory disease, a metabolic disease, or an autoimmune disease.

In addition, the present invention provides the use of the BMP-9 variant or the BMP-9 variant-Fc fusion protein for the manufacture of a medicament for the treatment of a tumor, an inflammatory disease, a metabolic disease, or an autoimmune disease.

DETAILED DESCRIPTION AND PREFERRED EMBODIMENTS OF THE INVENTION

Figure 1:
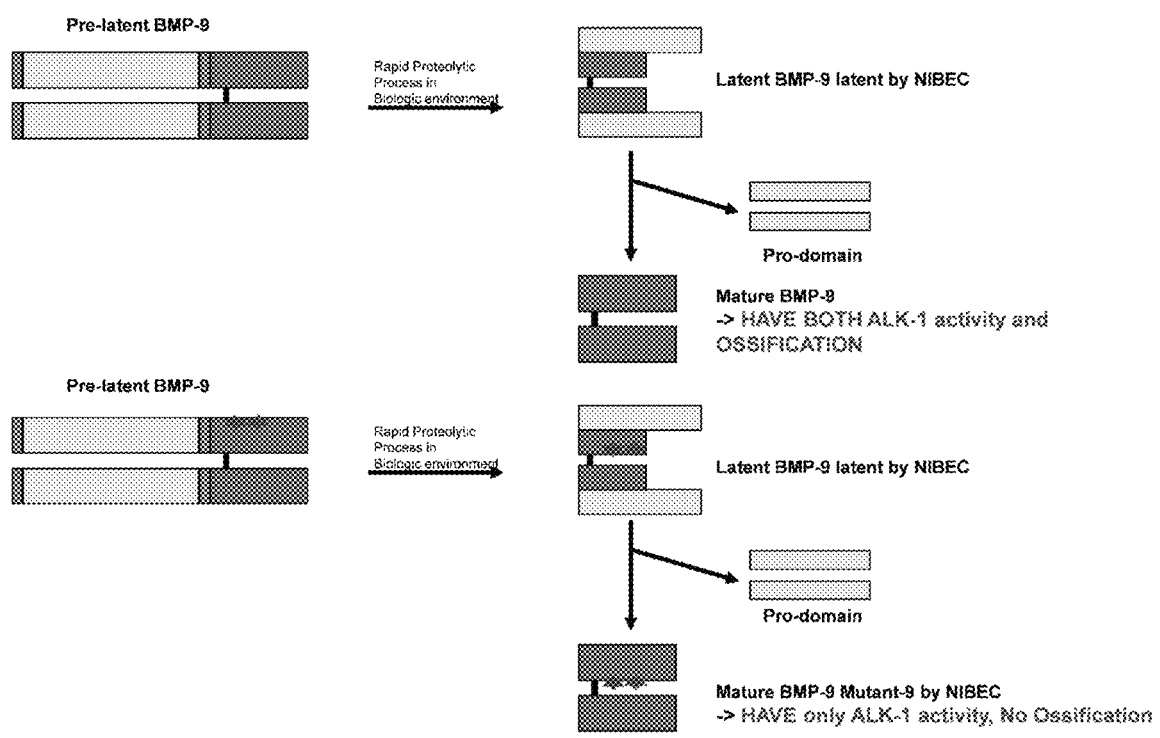
FIG. 1 schematically shows the outline of the present invention.

Unless otherwise defined, all technical and scientific terms used herein have the same meanings as those typically understood by those skilled in the art to which the present invention belongs. In general, the nomenclature used herein and test methods described below are well known in the art and are typical.

In the present invention, a BMP-9 gene was cloned and various variants thereof were produced and then expressed and purified in mammalian cells (CHO cells and human fetal kidney cell lines), and thus a BMP-9 variant that is effective for tumors, inflammatory diseases, cardiovascular diseases, metabolic diseases, and autoimmune diseases was selected, and was fused with Fc, thus increasing the blood half-life thereof. Specifically, in the present invention, BMP-9 was designed to induce the optimal therapeutic effect by regulating the ability to bind to receptors through substitution of one or several amino acids in the amino acid sequences corresponding to the wrist epitope and the knuckle epitope thereamong. The present invention was intended to select a variant capable of suppressing ectopic ossification to one-tenth or less while maintaining endothelial-cell-specific signaling, and it was confirmed that the variant according to the present invention greatly reduced ectopic ossification in mouse myoblasts (C2C12) compared to the wild type through alkaline phosphatase activity and alizarin red staining.

Accordingly, an aspect of the present invention pertains to bone morphogenetic protein-9 (BMP-9) or a variant thereof represented by any one amino acid sequence selected from the group consisting of SEQ ID NOS: 1 to 29, and another aspect of the present invention pertains to a BMP-9 variant-Fc fusion protein in which an Fc fragment of an immunoglobulin is linked to the bone morphogenetic protein-9 (BMP-9) or the variant thereof.

The amino acid sequence of SEQ ID NO: 1 represents wild-type BMP-9, which comprises both the signal sequence in bold and the sequence of Pro-BMP-9 underlined as represented below. Among them, the sequence of FFP-LADDVTPTKHAIVQTLVHLKE (SEQ ID NO: 29) is a region that binds to ALK-1 and belongs to the wrist epitope when viewed from the overall BMP-9 structure, and the sequence of KVGKACCVPTKLSPISVLYK (SEQ ID NO: 34) belongs to the knuckle epitope that binds to the BMP-2 receptor.

SEQ ID NO: 1

MAWVWTLLFLMAAAQSIQAKPLQSWGRGSAGGNAHSPLGVPGGGLPEHTF

NLKMFLENVKVDFLRSLNLSGVPSQDKTRVEPPQYMIDLYNRYTSDKSTT

PASNIVRSFSMEDAISITATEDFPFQKHILLFNISIPRHEQITRAELRLY

VSCQNHYDPSHDLKGSVVIYDYLDGTDAWDSATETKIFLVSQDIQDEGWE

TLEVSSAVKRWVRSDSTKSKNKLEVTVESHRKGCDTLDISVPPGSRNLPF

FVVFSNDHSSGTKETRLELREMISHEQESVLKKLSKDGSTEAGESSHEED

TDGHVAAGSTLARRKRSAGAGSHCQKTSLRVNFEDIGWDSWIIAPKEYEA

YECKGGCFFPLADDVTPTKHAIVQTLVHLKFPTKVGKACCVPTKLSPISV

LYKDDNGVPTLKYHYEGMSVAECGCR

The variant sequence derived from the wild-type BMP-9 sequence may be represented by any one amino acid sequence selected from SEQ ID NOs: 2 to 29, and these variants are configured such that some amino acid sequences are substituted in the wild-type BMP-9 sequence. However, the variant according to the present invention is not limited to the specific amino acid sequence represented by the sequence ID number, and also, an amino acid sequence that may be considered equivalent to the corresponding amino acid sequence falls within the scope of the present invention, as will be apparent to those skilled in the art. For example, when the 335$^{th}$ amino acid in SEQ ID NO: 2 is substituted with Ala, rather than Asp, compared to the wild type, so long as some of the sequences except for the core configuration of the variant are mutated so as not to affect the protein function and structure of BMP-9, the corresponding variant also falls within the scope of the present invention, as will be apparent to those skilled in the art. Accordingly, variants having at least 95%, at least 90%, at least 80%, or at least 70% homology with the remaining sequence other than the substitution of amino acids that are the core of the variant in any one amino acid sequence selected from SEQ ID NOs: 2 to 29 are understood to fall within the scope of the present invention.

Also, the variant of the present invention may be applied to other subtypes of bone morphogenetic protein, for example, BMP-7 or BMP-10.

In the present invention, in order to increase the blood half-life of wild-type or variant BMP-9, an Fc fragment of an immunoglobulin may be fused thereto. The Fc fragment of the immunoglobulin may be represented by the amino acid sequence of SEQ ID NO: 30, but is not limited thereto. In addition to the Fc fragment of the immunoglobulin, various peptides or proteins, such as albumin, may be fused thereto to increase the blood half-life of the protein.

In the present invention, the Fc fragment of the immunoglobulin may be linked to the N-terminus or C-terminus of the bone morphogenetic protein-9 (BMP-9) or the variant thereof.

In the present invention, the bone morphogenetic protein-9 (BMP-9) or the variant thereof and the Fc fragment of the immunoglobulin may be linked to each other via a linker, but the present invention is not limited thereto.

In the present invention, the linker may be represented by the amino acid sequence of SEQ ID NO: 31, but is not limited thereto.

In the present invention, the BMP-9 variant-Fc fusion protein may be represented by the amino acid sequence of SEQ ID NO: 32 or SEQ ID NO: 33, but is not limited thereto.

The BMP-9 or the variant thereof, or the fusion protein thereof according to the present invention may be used as a therapeutic, diagnostic, or research reagent, but is most preferably used for therapeutic purposes.

Specifically, the present invention provides a pharmaceutical composition for treating a tumor comprising the bone morphogenetic protein-9 (BMP-9) or the variant thereof, or the BMP-9 variant-Fc fusion protein, as an active ingredient.

In the present invention, the tumor may be at least one selected from the group consisting of breast cancer, lung cancer, colorectal cancer, colon cancer, liver cancer, pancreatic cancer, brain tumor, prostate cancer, skin cancer, osteosarcoma, and blood cancer, but is not limited thereto.

The present invention also provides a pharmaceutical composition for treating an inflammatory disease comprising the bone morphogenetic protein-9 (BMP-9) or the variant thereof, or the BMP-9 variant-Fc fusion protein, as an active ingredient.

In the present invention, the inflammatory disease may be at least one selected from the group consisting of steatohepatitis, hepatitis, and enteritis, but is not limited thereto.

The present invention also provides a pharmaceutical composition for treating a metabolic disease comprising the bone morphogenetic protein-9 (BMP-9) or the variant thereof, or the BMP-9 variant-Fc fusion protein, as an active ingredient.

In the present invention, the metabolic disease may be at least one selected from the group consisting of obesity, weight loss, diabetes, atherosclerosis, arteriosclerosis, cardiopulmonary disease, neurological disease, Alzheimer's disease, cognitive impairment, oxidative stress, skin disease, skin aging, damage caused by UV irradiation, hypertension, hypercholesterolemia (LDL, HDL, VLDL), hyperlipidemia (triglyceride), immunodeficiency, cancer, and metabolic syndrome, but is not limited thereto.

In the present invention, the cardiopulmonary disease may be at least one selected from the group consisting of myocardial infarction, hypertension, pulmonary arterial hypertension, myocardial fibrosis, and pulmonary fibrosis, but is not limited thereto.

The present invention also provides a pharmaceutical composition for treating an autoimmune disease comprising the bone morphogenetic protein-9 (BMP-9) or the variant thereof, or the BMP-9 variant-Fc fusion protein, as an active ingredient.

In the present invention, the autoimmune disease may be at least one selected from the group consisting of insulin-dependent diabetes, multiple sclerosis, autoimmune encephalomyelitis, rheumatoid arthritis, osteoarthritis, myasthenia gravis, thyroiditis, uveitis, Hashimoto's thyroiditis, thyrotoxicosis, pernicious anemia, autoimmune atrophic gastritis, autoimmune hemolytic anemia, idiopathic leukopenia, primary sclerosing cholangitis, alcoholic/nonalcoholic steatohepatitis, inflammatory bowel disease, Crohn's disease, ulcerative bowel disease, psoriasis, Sjogren's syndrome, scleroderma, Wegener's granulomatosis, polymyositis, dermatomyositis, discoid LE, and systemic lupus erythematosus, but is not limited thereto.

For the therapeutic purpose, the active BMP-9 variant according to the present invention or the derivative thereof may be administered alone, but is preferably administered in the form of a pharmaceutical composition (formulation), more preferably a sterile formulation.

In the present invention, the pharmaceutical composition may be formulated in any one dosage form selected from the group consisting of injectable preparations, oral preparations, liquids (e.g. for injection) such as aqueous solutions, suspensions, emulsions, etc., capsules, granules, tablets, and mucosal administration preparations, but the present invention is not limited thereto. These formulations may be prepared through a method used for typical formulation in the art for a method disclosed in Remington's Pharmaceutical Science (latest edition), Mack Publishing Company, Easton PA, and may be prepared into various formulations on individual depending diseases or components.

Also, the pharmaceutical composition of the present invention may further comprise at least one pharmaceutically acceptable carrier in addition to the therapeutic BMP-9 variant or the derivative thereof. The pharmaceutically acceptable carrier may be selected from among saline, sterile water, Ringer's solution, buffered saline, dextrose solution, maltodextrin solution, glycerol, ethanol, and mixtures of one or more thereof.

The pharmaceutical composition of t the present invention may further comprise a pharmaceutically acceptable adjuvant, as necessary. The adjuvant may be at least one selected from the group consisting of excipients, diluents, dispersants, buffers, antimicrobial preservatives, bacteriostats, surfactants, binders, lubricants, antioxidants, thickeners, and viscosity modifiers, but is not limited thereto.

The pharmaceutical composition according to the present invention may be administered orally or parenterally (e.g. intravenously, subcutaneously, intramuscularly, intraperitoneally, or topically) depending on a desired method, and the dosage thereof may be variously changed and applied depending on the patient's weight, age, gender, health status, and diet, administration time, administration method, excretion rate, and severity of disease according to the opinion of an expert.

In an embodiment of the present invention, a single dosage of the protein may be 1 μg/kg to 100 mg/kg, preferably 5 μg/kg to 50 mg/kg, and the protein may be administered once a day or 1-3 times a week, but the dosage and administration interval are not limited thereto.

Still another aspect of the present invention pertains to a method of preventing or treating a tumor, an inflammatory disease, a metabolic disease, or an autoimmune disease, comprising administering the BMP-9 variant or the BMP-9 variant-Fc fusion protein.

Yet another aspect of the present invention pertains to the use of the BMP-9 variant or the BMP-9 variant-Fc fusion protein for the prevention or treatment of a tumor, an inflammatory disease, a metabolic disease, or an autoimmune disease.

Still yet another aspect of the present invention relates to the use of the BMP-9 variant or the BMP-9 variant-Fc fusion protein for the manufacture of a medicament for the treatment of a tumor, an inflammatory disease, a metabolic disease, or an autoimmune disease.

EXAMPLES

A better understanding of the present invention may be obtained through the following examples. These examples are merely set forth to illustrate the present invention, and are not to be construed as limiting the scope of the present invention, as will be apparent to those skilled in the art.

Example 1. Construction of Recombinant Human proBMP-9 and proBMP-10

Figure 2:
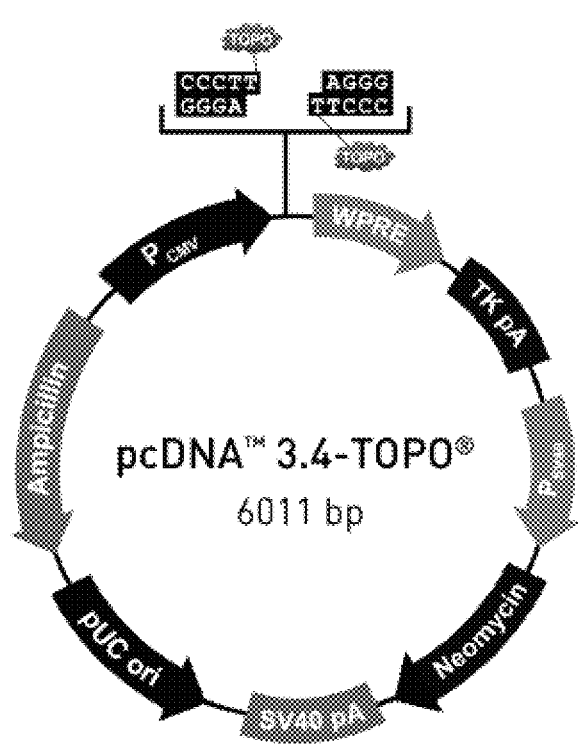
FIG. 2 shows an expression vector into which BMP-9, a BMP-9 variant, and Fc-fused BMP-9 are introduced.
Figure 3A:
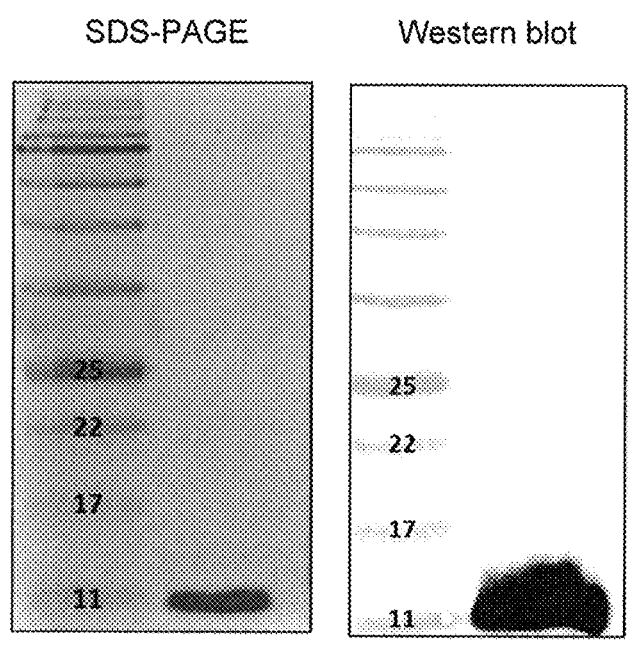
FIG. 3a shows results of SDS-PAGE and western blot of the expressed and purified BMP-9 variant.
Figure 3B:
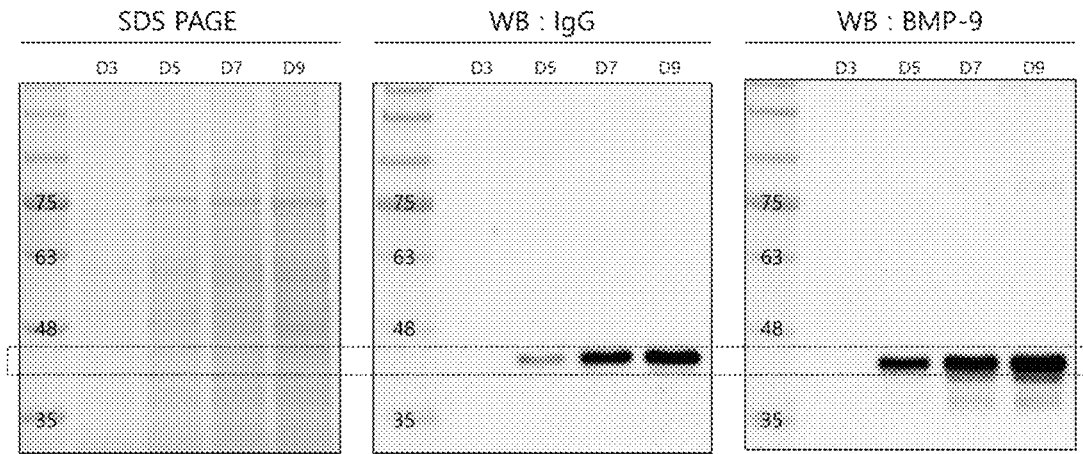
FIG. 3b shows results of SDS-PAGE and western blot of the expressed and purified Fc-fused BMP-9.

The entire range of cDNA including the open reading frame of human pre-proBMP9 was inserted and cloned into a pcDNA3.4 vector (FIG. 2), which was confirmed by DNA sequencing. The variant of proBMP9 was obtained using the QuickChange Site-directed mutagenesis kit, which was also confirmed by DNA sequencing.

BMP-9 wild-type and variant sequences used in the present invention are as follows.

```
                                          SEQ ID NO: 1
wild-type latent BMP-9 (NIBEC-J)
MAWVWTLLFLMAAAQSIQAKPLQSWGRGSAGGNAHSPLGVPGGGLPEHTF

NLKMFLENVKVDFLRSLNLSGVPSQDKTRVEPPQYMIDLYNRYTSDKSTT

PASNIVRSFSMEDAISITATEDFPFQKHILLFNISIPRHEQITRAELRLY

VSCQNHVDPSHDLKGSVVIYDVLDGTDAWDSATETKTFLVSQDIQDEGWE

TLEVSSAVKRWVRSDSTKSKNKLEVTVESHRKGCDTLDISVPPGSRNLPF

FVVFSNDHSSGTKETRLELREMISHEQESVLKKLSKDGSTEAGESSHEED

TDGHVAAGSTLARRKRSAGAGSHCQKTSLRVNFEDIGWDSWIIAPKEYEA

YECKGGCFFPLADDVTPTKHAIVQTLVHLKFPTKVGKACCVPTKLSPISV

LYKDDNGVPTLKYHYEGMSVAECGCR.
```

In the wild-type sequence, the signal peptide sequence is represented in bold, the Pro-BMP sequence is underlined, and the BMP-9 sequence is unmarked.

The plasmid containing pre-proBMP9 was transfected with polyethyleneimine into a CHO-S cell line, and an enhancer was then added thereto, followed by culture for 8 days. The expressed proBMP9 and proBMP10 were measured using an antiBMP9 antibody and an antiBMP10 antibody through a western blot method.

The expressed protein was isolated through a Q-Sepharose column that had already reached equilibrium using 1-5 L of conditioned medium as a buffer. The target protein attached to the column was subjected to fractionation by a sodium chloride gradient, and the fractionated sample was concentrated and then subjected to gel chromatography to obtain a target molecular weight. The protein thus obtained was confirmed to have a purity of 95% or more.

Example 2. Construction of Recombinant Human proBMP-9 Variants

BMP-9 or BMP-10 selectively binds to the ALK1 receptor in vascular endothelial cells, and thus, is promising as a therapeutic agent for cardiovascular diseases. However, they still have the potential to stimulate ossification by stimulating mesenchymal cells or myoblasts. When developing a therapeutic agent, it is necessary to incapacitate such potential. To date, it is not known which receptors are involved in the osteogenic differentiation capacity of BMP-9 or BMP-10. The researchers of the present invention have identified that the wrist epitope and the knuckle epitope in the structure of BMP-9 act as ligands for mediating major signaling, confirming that, by regulating these sequences, osteogenic differentiation capacity can be suppressed while maintaining endothelial cell signaling (SEQ ID NOS: 1-29, FIGS. 4*a* and 4*b*). These variants were determined to have similar physiological activities in vivo, and were expected to provide the advantage of enhancing the therapeutic effect while minimizing concerns about side effects.

Example 3. Signaling by BMP-9 Variants and Derivatives in Endothelial Cells

The amount of each proBMP9 variant was measured through ELISA and cells were treated therewith. In a serum-free state, the variant derived above was added to HUVEC cells in the indicated concentration range. After 8 hours of treatment, the cells were harvested, mRNA was extracted therefrom, and the expression of ID1 and BMPR-II was measured through quantitative PCR. In addition, for the expression of pSmad1/5/8, the cells were treated with the BMP-9 variant in a serum-free state, and after 1 hour, the results thereof were observed. The expression level of the protein obtained after treatment of the cells in a lysis buffer was measured through immunoblotting against the anti-pSmad1/5/8 antibody. Based on the results of observation (FIGS. 4*a* and 4*b*), it was confirmed that the variants significantly increased the expression of ID1 and BMPR-II, and the increased amount did not show a great difference compared to the wild-type BMP-9. As seen in previous reports, BMP-9 or BMP-10 was confirmed to act as ligands of ALK1 receptors in vascular endothelial cells. According to literature, BMP-9 is known to inhibit endothelial cell migration, proliferation, and angiogenesis by endothelial cells in the circulatory system.

Figure 4A:
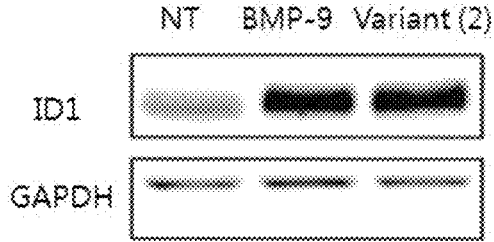
FIGS. 4a and 4b show signaling activity (FIG. 4a) and ossification signaling activity (FIG. 4b) of the expressed and purified BMP-9 and variants on vascular endothelial cells.
Figure 4B:
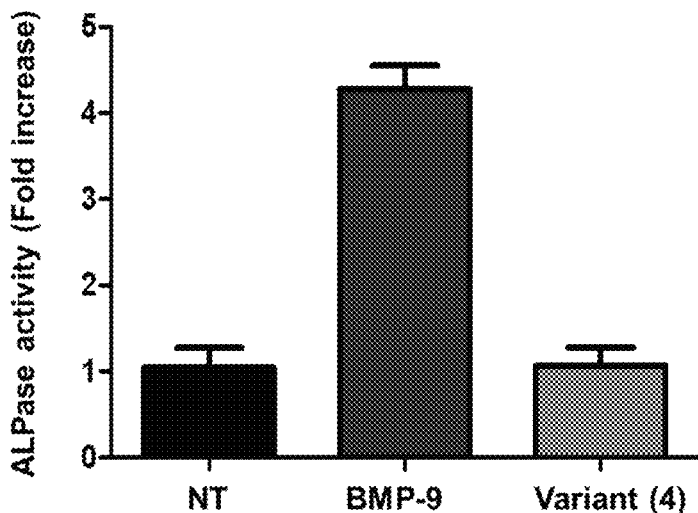

Example 4. Osteogenic Differentiation Signaling by BMP-9 Variants in C2C12 Cell Culture C2C12, a mouse myoblast, was selected to observe osteogenic differentiation capacity because it has differentiation ability similar to that of mesenchymal stem cells. C2C12 cells were cultured for 16 hours in DMEM containing 0.25% FBS and then treated with BMP-9 variants. After further culture for 72 hours, the cells were lysed with 1% Triton X-100/PBS, and the resulting protein was measured for ALP enzyme activity. ALP enzyme activity was determined by measuring absorbance at 405 nm of a water-soluble material produced by reacting with a 4-nitrophenyl phosphate disodium salt, which is substrate of the enzyme, and BMP-9 was purchased as a standard material and compared therewith. Based on the results of observation, it was confirmed that the variants had greatly lowered osteogenic differentiation capacity compared to the standard material (FIGS. 4*a* and 4*b*). The variants thus formed were judged to provide a therapeutic effect and also to have no side effects of ectopic ossification, by incapacitating ossification while maintaining the vascular endothelial cell signaling in Example 3.

Example 5. Effect of Prolonging Half-Life of BMP-9-Fc Derivative In Vivo

Figure 5:
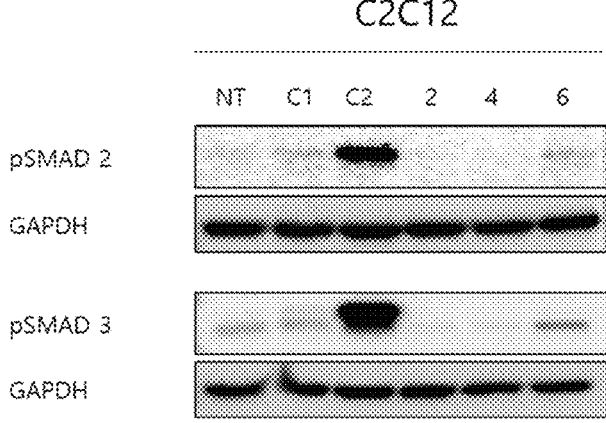
FIG. 5 shows effects of BMP-9 variants on inhibiting fibrosis-related markers in myoblasts.
Figure 6:
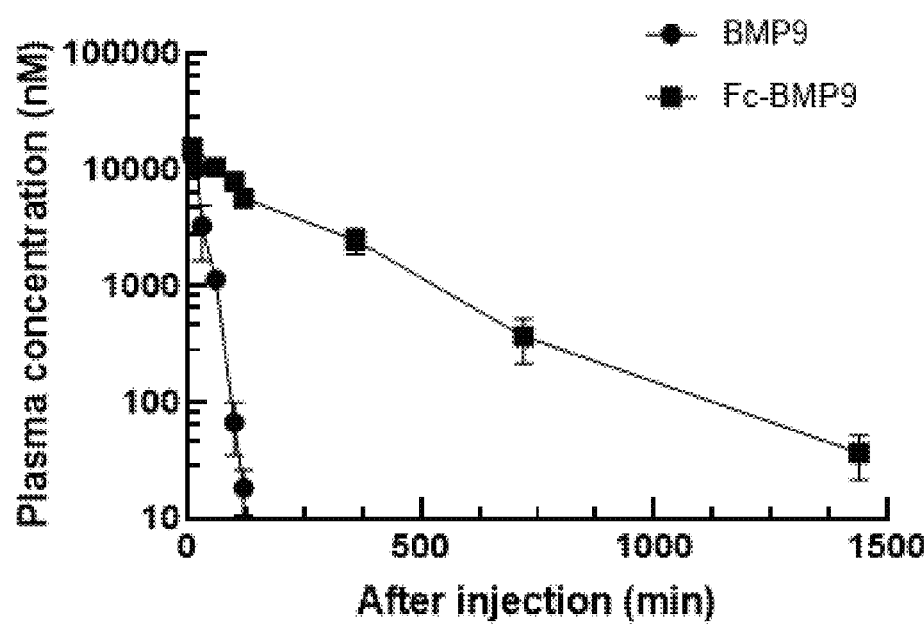
FIG. 6 is a graph showing results of measurement of blood concentrations of purified BMP-9 and Fc-fused BMP-9.

Each of BMP-9 and Fc-fused BMP-9 derivative was injected at a dose of 1 mg/kg through the tail vein of mice, blood was collected at regular time intervals, and the amount of BMP-9 in the blood was measured using a BMP-9 quantitative kit. Based on the results of measurement (FIG. 5), the Fc-bound BMP-9 derivative (SEQ ID NOS: 32-33) showed a greatly increased blood concentration curve.

Although specific embodiments of the present invention have been disclosed in detail above, it will be obvious to those skilled in the art that the description is merely of preferable exemplary embodiments and is not to be construed as limiting the scope of the present invention. Therefore, the substantial scope of the present invention will be defined by the appended claims and equivalents thereto.

INDUSTRIAL APPLICABILITY

According to the present invention, a variant was designed so as to maximize the therapeutic effect of BMP-9 and greatly reduce side effects thereof, and was expressed and purified with high efficiency in mammalian cells. Moreover, in order to extend the blood half-life of BMP-9, a fusion protein fused with the Fc region of immunoglobulin was additionally constructed. Such a variant and fusion protein can exhibit superior therapeutic effects on various diseases such as tumors, fibrosis, cardiopulmonary vascular disease, obesity, and fatty liver in vitro and through animal experimentation, and thus can be expected to be useful as novel therapeutic agents for the treatment of these diseases.

SEQUENCE LIST FREE TEXT

An electronic file is attached.

---

The invention claimed is:

1. A bone morphogenetic protein-9 (BMP-9) variant represented by any one amino acid sequence selected from the group consisting of SEQ ID NOs: 2 to 28.

2. A BMP-9 variant-Fc fusion protein in which an Fc fragment of an immunoglobulin is linked to the BMP-9 variant according to claim 1.

3. The BMP-9 variant-Fc fusion protein according to claim 2, wherein the Fc fragment of the immunoglobulin is represented by the amino acid sequence of SEQ ID NO: 30.

4. The BMP-9 variant-Fc fusion protein according to claim 2, wherein the BMP-9 variant and the Fc fragment of the immunoglobulin are linked to each other via a linker.

5. The BMP-9 variant-Fc fusion protein according to claim 4, wherein the linker is represented by the amino acid sequence of SEQ ID NO: 31.

6. A pharmaceutical composition comprising the BMP-9 variant according to claim 1 or the BMP-9 variant-Fc fusion protein according to claim 2 as an active ingredient.

7. The composition according to claim 6, comprising a pharmaceutically acceptable carrier.

8. The composition according to claim 7, wherein the pharmaceutically acceptable carrier is selected from among saline, sterile water, Ringer's solution, buffered saline, dextrose solution, maltodextrin solution, glycerol, ethanol, and mixtures of one or more thereof.

9. The composition according to claim 6, comprising a pharmaceutically acceptable adjuvant.

10. The composition according to claim 9 comprising at least one selected from the group consisting of excipients, diluents, dispersants, buffers, antimicrobial preservatives, bacteriostats, surfactants, binders, lubricants, antioxidants, thickeners, and viscosity modifiers.

* * * * *

```
                         SEQUENCE LISTING

<160> NUMBER OF SEQ ID NOS: 34

<210> SEQ ID NO 1
<211> LENGTH: 426
<212> TYPE: PRT
<213> ORGANISM: Artificial Sequence
<220> FEATURE:
<223> OTHER INFORMATION: Synthetic construct

<400> SEQUENCE: 1

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
            35                  40                  45
```

-continued

```
Thr Phe Asn Leu Lys Met Phe Leu Glu Asn Val Lys Val Asp Phe Leu
    50              55              60

Arg Ser Leu Asn Leu Ser Gly Val Pro Ser Gln Asp Lys Thr Arg Val
65              70              75              80

Glu Pro Pro Gln Tyr Met Ile Asp Leu Tyr Asn Arg Tyr Thr Ser Asp
            85              90              95

Lys Ser Thr Thr Pro Ala Ser Asn Ile Val Arg Ser Phe Ser Met Glu
            100             105             110

Asp Ala Ile Ser Ile Thr Ala Thr Glu Asp Phe Pro Phe Gln Lys His
            115             120             125

Ile Leu Leu Phe Asn Ile Ser Ile Pro Arg His Glu Gln Ile Thr Arg
    130             135             140

Ala Glu Leu Arg Leu Tyr Val Ser Cys Gln Asn His Val Asp Pro Ser
145             150             155             160

His Asp Leu Lys Gly Ser Val Val Ile Tyr Asp Val Leu Asp Gly Thr
            165             170             175

Asp Ala Trp Asp Ser Ala Thr Glu Thr Lys Thr Phe Leu Val Ser Gln
            180             185             190

Asp Ile Gln Asp Glu Gly Trp Glu Thr Leu Glu Val Ser Ser Ala Val
            195             200             205

Lys Arg Trp Val Arg Ser Asp Ser Thr Lys Ser Lys Asn Lys Leu Glu
    210             215             220

Val Thr Val Glu Ser His Arg Lys Gly Cys Asp Thr Leu Asp Ile Ser
225             230             235             240

Val Pro Pro Gly Ser Arg Asn Leu Pro Phe Phe Val Val Phe Ser Asn
            245             250             255

Asp His Ser Ser Gly Thr Lys Glu Thr Arg Leu Glu Leu Arg Glu Met
            260             265             270

Ile Ser His Glu Gln Glu Ser Val Leu Lys Lys Leu Ser Lys Asp Gly
    275             280             285

Ser Thr Glu Ala Gly Glu Ser Ser His Glu Glu Asp Thr Asp Gly His
    290             295             300

Val Ala Ala Gly Ser Thr Leu Ala Arg Arg Lys Arg Ser Ala Gly Ala
305             310             315             320

Gly Ser His Cys Gln Lys Thr Ser Leu Arg Val Asn Phe Glu Asp Ile
            325             330             335

Gly Trp Asp Ser Trp Ile Ile Ala Pro Lys Glu Tyr Glu Ala Tyr Glu
            340             345             350

Cys Lys Gly Gly Cys Phe Phe Pro Leu Ala Asp Asp Val Thr Pro Thr
            355             360             365

Lys His Ala Ile Val Gln Thr Leu Val His Leu Lys Phe Pro Thr Lys
    370             375             380

Val Gly Lys Ala Cys Cys Val Pro Thr Lys Leu Ser Pro Ile Ser Val
385             390             395             400

Leu Tyr Lys Asp Asp Met Gly Val Pro Thr Leu Lys Tyr His Tyr Glu
            405             410             415

Gly Met Ser Val Ala Glu Cys Gly Cys Arg
            420             425
```

<210> SEQ ID NO 2
<211> LENGTH: 426
<212> TYPE: PRT
<213> ORGANISM: Artificial Sequence
<220> FEATURE:
<223> OTHER INFORMATION: Synthetic construct

```
<400> SEQUENCE: 2

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
            85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
        115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
            165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
        195                 200                 205

Lys Arg Trp Val Arg Ser Asp Ser Thr Lys Ser Lys Asn Lys Leu Glu
    210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
            245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Ala Ile
            325                 330                 335

Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys His Ala Ile Val Gln Thr Leu Val His Leu Lys Phe Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
```

```
                  405              410              415

Gly Met Ser Val Ala Glu Cys Gly Cys Arg
        420              425

<210> SEQ ID NO 3
<211> LENGTH: 426
<212> TYPE: PRT
<213> ORGANISM: Artificial Sequence
<220> FEATURE:
<223> OTHER INFORMATION: Synthetic construct

<400> SEQUENCE: 3

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
        115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
        195                 200                 205

Lys Arg Trp Val Arg Ser Asp Ser Thr Lys Ser Lys Asn Lys Leu Glu
    210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Glu Trp Asp Ser Trp Ile Ile Ala Pro Lys Glu Tyr Glu Ala Tyr Glu
```

-continued

<pre>
                340                 345                 350

Cys Lys Gly Gly Cys Phe Phe Pro Leu Ala Asp Asp Val Thr Pro Thr
            355                 360                 365

Lys His Ala Ile Val Gln Thr Leu Val His Leu Lys Phe Pro Thr Lys
        370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425

<210> SEQ ID NO 4
<211> LENGTH: 426
<212> TYPE: PRT
<213> ORGANISM: Artificial Sequence
<220> FEATURE:
<223> OTHER INFORMATION: Synthetic construct

<400> SEQUENCE: 4

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
        130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
        195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
</pre>

```
                    275                    280                    285
Ser Thr Glu Ala Gly Glu Ser Ser His Glu Glu Asp Thr Asp Gly His
    290                    295                    300
Val Ala Ala Gly Ser Thr Leu Ala Arg Arg Lys Arg Ser Ala Gly Ala
305                    310                    315                    320
Gly Ser His Cys Gln Lys Thr Ser Leu Arg Val Asn Phe Glu Asp Ile
                    325                    330                    335
Gly Trp Asp Ser Trp Ile Ile Ala Pro Lys Glu Tyr Glu Ala Tyr Glu
                    340                    345                    350
Cys Lys Gly Gly Cys Phe Phe Pro Leu Ala Asp Glu Val Thr Pro Thr
                    355                    360                    365
Lys His Ala Ile Val Gln Thr Leu Val His Leu Lys Phe Pro Thr Lys
    370                    375                    380
Val Gly Lys Ala Cys Cys Val Pro Thr Lys Leu Ser Pro Ile Ser Val
385                    390                    395                    400
Leu Tyr Lys Asp Asp Met Gly Val Pro Thr Leu Lys Tyr His Tyr Glu
                    405                    410                    415
Gly Met Ser Val Ala Glu Cys Gly Cys Arg
                    420                    425

<210> SEQ ID NO 5
<211> LENGTH: 426
<212> TYPE: PRT
<213> ORGANISM: Artificial Sequence
<220> FEATURE:
<223> OTHER INFORMATION: Synthetic construct

<400> SEQUENCE: 5

Met Ala Trp Val Trp Thr Leu Leu Phe Leu Met Ala Ala Ala Gln Ser
1                   5                    10                   15
Ile Gln Ala Lys Pro Leu Gln Ser Trp Gly Arg Gly Ser Ala Gly Gly
                    20                   25                   30
Asn Ala His Ser Pro Leu Gly Val Pro Gly Gly Gly Leu Pro Glu His
            35                   40                   45
Thr Phe Asn Leu Lys Met Phe Leu Glu Asn Val Lys Val Asp Phe Leu
    50                   55                   60
Arg Ser Leu Asn Leu Ser Gly Val Pro Ser Gln Asp Lys Thr Arg Val
65                   70                   75                   80
Glu Pro Pro Gln Tyr Met Ile Asp Leu Tyr Asn Arg Tyr Thr Ser Asp
                    85                   90                   95
Lys Ser Thr Thr Pro Ala Ser Asn Ile Val Arg Ser Phe Ser Met Glu
                100                  105                  110
Asp Ala Ile Ser Ile Thr Ala Thr Glu Asp Phe Pro Phe Gln Lys His
            115                  120                  125
Ile Leu Leu Phe Asn Ile Ser Ile Pro Arg His Glu Gln Ile Thr Arg
    130                  135                  140
Ala Glu Leu Arg Leu Tyr Val Ser Cys Gln Asn His Val Asp Pro Ser
145                  150                  155                  160
His Asp Leu Lys Gly Ser Val Val Ile Tyr Asp Val Leu Asp Gly Thr
                165                  170                  175
Asp Ala Trp Asp Ser Ala Thr Glu Thr Lys Thr Phe Leu Val Ser Gln
            180                  185                  190
Asp Ile Gln Asp Glu Gly Trp Glu Thr Leu Glu Val Ser Ser Ala Val
            195                  200                  205
Lys Arg Trp Val Arg Ser Asp Ser Thr Lys Ser Lys Asn Lys Leu Glu
```

-continued

```
            210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
                260                 265                 270

Ile Ser His Glu Gln Glu Ser Val Leu Lys Lys Leu Ser Lys Asp Gly
            275                 280                 285

Ser Thr Glu Ala Gly Glu Ser Ser His Glu Glu Asp Thr Asp Gly His
            290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
                340                 345                 350

Cys Lys Gly Gly Cys Phe Phe Pro Leu Ala Asp Asp Val Thr Pro Thr
                355                 360                 365

Lys His Asp Ile Val Gln Thr Leu Val His Leu Lys Phe Pro Thr Lys
            370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425
```

```
<210> SEQ ID NO 6
<211> LENGTH: 426
<212> TYPE: PRT
<213> ORGANISM: Artificial Sequence
<220> FEATURE:
<223> OTHER INFORMATION: Synthetic construct

<400> SEQUENCE: 6

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
                20                  25                  30

Asn Ala His Ser Pro Leu Gly Val Pro Gly Gly Gly Leu Pro Glu His
            35                  40                  45

Thr Phe Asn Leu Lys Met Phe Leu Glu Asn Val Lys Val Asp Phe Leu
            50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
                100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
            130                 135                 140

Ala Glu Leu Arg Leu Tyr Val Ser Cys Gln Asn His Val Asp Pro Ser
```

-continued

```
         145                 150                 155                 160

His Asp Leu Lys Gly Ser Val Val Ile Tyr Asp Val Leu Asp Gly Thr
                 165                 170                 175

Asp Ala Trp Asp Ser Ala Thr Glu Thr Lys Thr Phe Leu Val Ser Gln
                 180                 185                 190

Asp Ile Gln Asp Glu Gly Trp Glu Thr Leu Glu Val Ser Ser Ala Val
                 195                 200                 205

Lys Arg Trp Val Arg Ser Asp Ser Thr Lys Ser Lys Asn Lys Leu Glu
         210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                 245                 250                 255

Asp His Ser Ser Gly Thr Lys Glu Thr Arg Leu Glu Leu Arg Glu Met
                 260                 265                 270

Ile Ser His Glu Gln Glu Ser Val Leu Lys Lys Leu Ser Lys Asp Gly
                 275                 280                 285

Ser Thr Glu Ala Gly Glu Ser Ser His Glu Glu Asp Thr Asp Gly His
         290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                 325                 330                 335

Gly Trp Asp Ser Trp Ile Ile Ala Pro Lys Glu Tyr Glu Ala Tyr Glu
                 340                 345                 350

Cys Lys Gly Gly Cys Phe Phe Pro Leu Ala Asp Asp Val Thr Pro Thr
                 355                 360                 365

Lys His Ala Ile Val Gln Thr Leu Val His Leu Lys Phe Pro Thr Lys
         370                 375                 380

Val Gly Lys Ala Cys Cys Val Pro Thr Lys Leu Ser Pro Ile Ser Val
385                 390                 395                 400

Leu Tyr Lys Asp Glu Met Gly Val Pro Thr Leu Lys Tyr His Tyr Glu
                 405                 410                 415

Gly Met Ser Val Ala Glu Cys Gly Cys Arg
                 420                 425
```

<210> SEQ ID NO 7
<211> LENGTH: 426
<212> TYPE: PRT
<213> ORGANISM: Artificial Sequence
<220> FEATURE:
<223> OTHER INFORMATION: Synthetic construct

<400> SEQUENCE: 7

```
Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
                20                  25                  30

Asn Ala His Ser Pro Leu Gly Val Pro Gly Gly Gly Leu Pro Glu His
         35                  40                  45

Thr Phe Asn Leu Lys Met Phe Leu Glu Asn Val Lys Val Asp Phe Leu
         50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
```

-continued

```
                  85                  90                  95
Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
        130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
                180                 185                 190

Asp Ile Gln Asp Glu Gly Trp Glu Thr Leu Glu Val Ser Ser Ala Val
                195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
            275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
            325                 330                 335

Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys His Ala Ile Val Gln Thr Leu Val His Leu Lys Phe Pro Thr Lys
        370                 375                 380

Val Gly Lys Ala Cys Cys Val Pro Thr Lys Leu Ser Pro Ile Ser Val
385                 390                 395                 400

Leu Tyr Lys Asp Asn Met Gly Val Pro Thr Leu Lys Tyr His Tyr Glu
                405                 410                 415

Gly Met Ser Val Ala Glu Cys Gly Cys Arg
                420                 425
```

```
<210> SEQ ID NO 8
<211> LENGTH: 426
<212> TYPE: PRT
<213> ORGANISM: Artificial Sequence
<220> FEATURE:
<223> OTHER INFORMATION: Synthetic construct

<400> SEQUENCE: 8

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
```

-continued

```
                20                25                30

Asn Ala His Ser Pro Leu Gly Val Pro Gly Gly Gly Leu Pro Glu His
        35                40                45

Thr Phe Asn Leu Lys Met Phe Leu Glu Asn Val Lys Val Asp Phe Leu
    50                55                60

Arg Ser Leu Asn Leu Ser Gly Val Pro Ser Gln Asp Lys Thr Arg Val
65                70                75                80

Glu Pro Pro Gln Tyr Met Ile Asp Leu Tyr Asn Arg Tyr Thr Ser Asp
                85                90                95

Lys Ser Thr Thr Pro Ala Ser Asn Ile Val Arg Ser Phe Ser Met Glu
                100               105               110

Asp Ala Ile Ser Ile Thr Ala Thr Glu Asp Phe Pro Phe Gln Lys His
        115               120               125

Ile Leu Leu Phe Asn Ile Ser Ile Pro Arg His Glu Gln Ile Thr Arg
        130               135               140

Ala Glu Leu Arg Leu Tyr Val Ser Cys Gln Asn His Val Asp Pro Ser
145               150               155               160

His Asp Leu Lys Gly Ser Val Val Ile Tyr Asp Val Leu Asp Gly Thr
                165               170               175

Asp Ala Trp Asp Ser Ala Thr Glu Thr Lys Thr Phe Leu Val Ser Gln
                180               185               190

Asp Ile Gln Asp Glu Gly Trp Glu Thr Leu Glu Val Ser Ser Ala Val
                195               200               205

Lys Arg Trp Val Arg Ser Asp Ser Thr Lys Ser Lys Asn Lys Leu Glu
        210               215               220

Val Thr Val Glu Ser His Arg Lys Gly Cys Asp Thr Leu Asp Ile Ser
225               230               235               240

Val Pro Pro Gly Ser Arg Asn Leu Pro Phe Phe Val Val Phe Ser Asn
                245               250               255

Asp His Ser Ser Gly Thr Lys Glu Thr Arg Leu Glu Leu Arg Glu Met
                260               265               270

Ile Ser His Glu Gln Glu Ser Val Leu Lys Lys Leu Ser Lys Asp Gly
        275               280               285

Ser Thr Glu Ala Gly Glu Ser Ser His Glu Glu Asp Thr Asp Gly His
        290               295               300

Val Ala Ala Gly Ser Thr Leu Ala Arg Arg Lys Arg Ser Ala Gly Ala
305               310               315               320

Gly Ser His Cys Gln Lys Thr Ser Leu Arg Val Asn Phe Glu Asp Ile
                325               330               335

Gly Trp Asp Ser Trp Ile Ile Ala Pro Lys Glu Tyr Glu Ala Tyr Glu
                340               345               350

Cys Lys Gly Gly Cys Phe Phe Pro Leu Ala Asp Asp Val Thr Pro Thr
                355               360               365

Lys His Ala Ile Val Gln Thr Leu Val His Leu Lys Phe Pro Thr Lys
        370               375               380

Val Gly Lys Ala Cys Cys Val Pro Thr Lys Leu Ser Pro Ile Ser Val
385               390               395               400

Leu Tyr Lys Asp Gln Met Gly Val Pro Thr Leu Lys Tyr His Tyr Glu
                405               410               415

Gly Met Ser Val Ala Glu Cys Gly Cys Arg
                420               425
```

<210> SEQ ID NO 9

-continued

```
<211> LENGTH: 426
<212> TYPE: PRT
<213> ORGANISM: Artificial Sequence
<220> FEATURE:
<223> OTHER INFORMATION: Synthetic construct

<400> SEQUENCE: 9

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
        130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys His Ala Ile Val Gln Thr Leu Val His Leu Lys Phe Pro Thr Lys
    370                 375                 380
```

```
Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Trp Glu
                405                 410                 415

Gly Met Ser Val Ala Glu Cys Gly Cys Arg
                420                 425

<210> SEQ ID NO 10
<211> LENGTH: 426
<212> TYPE: PRT
<213> ORGANISM: Artificial Sequence
<220> FEATURE:
<223> OTHER INFORMATION: Synthetic construct

<400> SEQUENCE: 10

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
                20                  25                  30

Asn Ala His Ser Pro Leu Gly Val Pro Gly Gly Gly Leu Pro Glu His
            35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
                100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
                180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
    210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
    275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320
```

-continued

```
Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
                340                 345                 350

Cys Lys Gly Gly Cys Phe Phe Pro Lys Ala Asp Asp Val Thr Pro Thr
            355                 360                 365

Lys His Ala Ile Val Gln Thr Leu Val His Leu Lys Phe Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425
```

<210> SEQ ID NO 11
<211> LENGTH: 426
<212> TYPE: PRT
<213> ORGANISM: Artificial Sequence
<220> FEATURE:
<223> OTHER INFORMATION: Synthetic construct

<400> SEQUENCE: 11

```
Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
                20                  25                  30

Asn Ala His Ser Pro Leu Gly Val Pro Gly Gly Gly Leu Pro Glu His
            35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
                100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
                180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
    210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255
```

```
Asp His Ser Ser Gly Thr Lys Glu Thr Arg Leu Glu Leu Arg Glu Met
        260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
        290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
        340                 345                 350

Cys Lys Gly Gly Cys Phe Phe Pro Leu Ala Asn Asp Val Thr Pro Thr
        355                 360                 365

Lys His Ala Ile Val Gln Thr Leu Val His Leu Lys Phe Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425
```

```
<210> SEQ ID NO 12
<211> LENGTH: 426
<212> TYPE: PRT
<213> ORGANISM: Artificial Sequence
<220> FEATURE:
<223> OTHER INFORMATION: Synthetic construct

<400> SEQUENCE: 12
```

```
Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
        115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
                180                 185                 190
```

-continued

```
Asp Ile Gln Asp Glu Gly Trp Glu Thr Leu Glu Val Ser Ser Ala Val
        195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
                260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
        290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
                340                 345                 350

Cys Lys Gly Gly Cys Phe Phe Pro Leu Ala Gln Asp Val Thr Pro Thr
        355                 360                 365

Lys His Ala Ile Val Gln Thr Leu Val His Leu Lys Phe Pro Thr Lys
        370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425
```

```
<210> SEQ ID NO 13
<211> LENGTH: 426
<212> TYPE: PRT
<213> ORGANISM: Artificial Sequence
<220> FEATURE:
<223> OTHER INFORMATION: Synthetic construct

<400> SEQUENCE: 13
```

```
Met Ala Trp Val Trp Thr Leu Leu Phe Leu Met Ala Ala Ala Gln Ser
1                   5                   10                  15

Ile Gln Ala Lys Pro Leu Gln Ser Trp Gly Arg Gly Ser Ala Gly Gly
                20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
        50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
                100                 105                 110

Asp Ala Ile Ser Ile Thr Ala Thr Glu Asp Phe Pro Phe Gln Lys His
        115                 120                 125
```

-continued

```
Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
                180                 185                 190

Asp Ile Gln Asp Glu Gly Trp Glu Thr Leu Glu Val Ser Ser Ala Val
                195                 200                 205

Lys Arg Trp Val Arg Ser Asp Ser Thr Lys Ser Lys Asn Lys Leu Glu
    210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
                260                 265                 270

Ile Ser His Glu Gln Glu Ser Val Leu Lys Lys Leu Ser Lys Asp Gly
    275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
                340                 345                 350

Cys Lys Gly Gly Cys Phe Phe Pro Leu Ala Asp Asp Val Thr Pro Thr
                355                 360                 365

Lys His Pro Ile Val Gln Thr Leu Val His Leu Lys Phe Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425
```

```
<210> SEQ ID NO 14
<211> LENGTH: 426
<212> TYPE: PRT
<213> ORGANISM: Artificial Sequence
<220> FEATURE:
<223> OTHER INFORMATION: Synthetic construct

<400> SEQUENCE: 14

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60
```

-continued

```
Arg Ser Leu Asn Leu Ser Gly Val Pro Ser Gln Asp Lys Thr Arg Val
65              70              75              80

Glu Pro Pro Gln Tyr Met Ile Asp Leu Tyr Asn Arg Tyr Thr Ser Asp
                85              90              95

Lys Ser Thr Thr Pro Ala Ser Asn Ile Val Arg Ser Phe Ser Met Glu
            100             105             110

Asp Ala Ile Ser Ile Thr Ala Thr Glu Asp Phe Pro Phe Gln Lys His
            115             120             125

Ile Leu Leu Phe Asn Ile Ser Ile Pro Arg His Glu Gln Ile Thr Arg
        130             135             140

Ala Glu Leu Arg Leu Tyr Val Ser Cys Gln Asn His Val Asp Pro Ser
145             150             155             160

His Asp Leu Lys Gly Ser Val Val Ile Tyr Asp Val Leu Asp Gly Thr
            165             170             175

Asp Ala Trp Asp Ser Ala Thr Glu Thr Lys Thr Phe Leu Val Ser Gln
            180             185             190

Asp Ile Gln Asp Glu Gly Trp Glu Thr Leu Glu Val Ser Ser Ala Val
            195             200             205

Lys Arg Trp Val Arg Ser Asp Ser Thr Lys Ser Lys Asn Lys Leu Glu
        210             215             220

Val Thr Val Glu Ser His Arg Lys Gly Cys Asp Thr Leu Asp Ile Ser
225             230             235             240

Val Pro Pro Gly Ser Arg Asn Leu Pro Phe Phe Val Val Phe Ser Asn
            245             250             255

Asp His Ser Ser Gly Thr Lys Glu Thr Arg Leu Glu Leu Arg Glu Met
            260             265             270

Ile Ser His Glu Gln Glu Ser Val Leu Lys Lys Leu Ser Lys Asp Gly
            275             280             285

Ser Thr Glu Ala Gly Glu Ser Ser His Glu Glu Asp Thr Asp Gly His
        290             295             300

Val Ala Ala Gly Ser Thr Leu Ala Arg Arg Lys Arg Ser Ala Gly Ala
305             310             315             320

Gly Ser His Cys Gln Lys Thr Ser Leu Arg Val Asn Phe Glu Asp Ile
            325             330             335

Gly Trp Asp Ser Trp Ile Ile Ala Pro Lys Glu Tyr Glu Ala Tyr Glu
            340             345             350

Cys Lys Gly Gly Cys Phe Phe Pro Leu Ala Asp Asp Val Thr Pro Thr
            355             360             365

Lys His Ala Arg Val Gln Thr Leu Val His Leu Lys Phe Pro Thr Lys
        370             375             380

Val Gly Lys Ala Cys Cys Val Pro Thr Lys Leu Ser Pro Ile Ser Val
385             390             395             400

Leu Tyr Lys Asp Asp Met Gly Val Pro Thr Leu Lys Tyr His Tyr Glu
            405             410             415

Gly Met Ser Val Ala Glu Cys Gly Cys Arg
            420             425
```

<210> SEQ ID NO 15
<211> LENGTH: 426
<212> TYPE: PRT
<213> ORGANISM: Artificial Sequence
<220> FEATURE:
<223> OTHER INFORMATION: Synthetic construct

<400> SEQUENCE: 15

-continued

```
Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
            165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
    210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
            245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
            275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
            325                 330                 335

Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys His Ala Ile Val Gln Thr Arg Val His Leu Lys Phe Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
            405                 410                 415
```

```
Gly Met Ser Val Ala Glu Cys Gly Cys Arg
        420             425

<210> SEQ ID NO 16
<211> LENGTH: 426
<212> TYPE: PRT
<213> ORGANISM: Artificial Sequence
<220> FEATURE:
<223> OTHER INFORMATION: Synthetic construct

<400> SEQUENCE: 16

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65              70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
        115                 120                 125

Ile Leu Leu Phe Asn Ile Ser Ile Pro Arg His Glu Gln Ile Thr Arg
        130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
            165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
            325                 330                 335

Gly Trp Asp Ser Trp Ile Ile Ala Pro Lys Glu Tyr Glu Ala Tyr Glu
            340                 345                 350
```

-continued

```
Cys Lys Gly Gly Cys Phe Phe Pro Leu Ala Asp Asp Val Thr Pro Thr
        355                 360                 365

Lys His His Lys Val Gln Thr Leu Val His Leu Lys Phe Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
            420                 425

<210> SEQ ID NO 17
<211> LENGTH: 426
<212> TYPE: PRT
<213> ORGANISM: Artificial Sequence
<220> FEATURE:
<223> OTHER INFORMATION: Synthetic construct

<400> SEQUENCE: 17

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
        115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
        195                 200                 205

Lys Arg Trp Val Arg Ser Asp Ser Thr Lys Ser Lys Asn Lys Leu Glu
    210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
            275                 280                 285
```

-continued

```
Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
                340                 345                 350

Cys Lys Gly Gly Cys Phe Phe Pro Leu Ala Asp Asp Val Thr Pro Thr
                355                 360                 365

Lys Arg Arg Lys Val Gln Thr Leu Val His Leu Lys Phe Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425
```

```
<210> SEQ ID NO 18
<211> LENGTH: 426
<212> TYPE: PRT
<213> ORGANISM: Artificial Sequence
<220> FEATURE:
<223> OTHER INFORMATION: Synthetic construct

<400> SEQUENCE: 18
```

```
Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
                20                  25                  30

Asn Ala His Ser Pro Leu Gly Val Pro Gly Gly Gly Leu Pro Glu His
            35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
                100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
    210                 215                 220
```

-continued

```
Val Thr Val Glu Ser His Arg Lys Gly Cys Asp Thr Leu Asp Ile Ser
225             230             235             240

Val Pro Pro Gly Ser Arg Asn Leu Pro Phe Phe Val Val Phe Ser Asn
            245             250             255

Asp His Ser Ser Gly Thr Lys Glu Thr Arg Leu Glu Leu Arg Glu Met
            260             265             270

Ile Ser His Glu Gln Glu Ser Val Leu Lys Lys Leu Ser Lys Asp Gly
        275             280             285

Ser Thr Glu Ala Gly Glu Ser Ser His Glu Glu Asp Thr Asp Gly His
    290             295             300

Val Ala Ala Gly Ser Thr Leu Ala Arg Arg Lys Arg Ser Ala Gly Ala
305             310             315             320

Gly Ser His Cys Gln Lys Thr Ser Leu Arg Val Asn Phe Glu Asp Ile
            325             330             335

Gly Trp Asp Ser Trp Ile Ile Ala Pro Lys Glu Tyr Glu Ala Tyr Glu
            340             345             350

Cys Lys Gly Gly Cys Phe Phe Pro Leu Ala Asp Asp Val Thr Pro Thr
            355             360             365

Lys His Arg Lys Val Arg Thr Arg Val His Leu Lys Phe Pro Thr Lys
    370             375             380

Val Gly Lys Ala Cys Cys Val Pro Thr Lys Leu Ser Pro Ile Ser Val
385             390             395             400

Leu Tyr Lys Asp Asp Met Gly Val Pro Thr Leu Lys Tyr His Tyr Glu
            405             410             415

Gly Met Ser Val Ala Glu Cys Gly Cys Arg
            420             425
```

```
<210> SEQ ID NO 19
<211> LENGTH: 426
<212> TYPE: PRT
<213> ORGANISM: Artificial Sequence
<220> FEATURE:
<223> OTHER INFORMATION: Synthetic construct

<400> SEQUENCE: 19

Met Ala Trp Val Trp Thr Leu Leu Phe Leu Met Ala Ala Ala Gln Ser
1               5               10              15

Ile Gln Ala Lys Pro Leu Gln Ser Trp Gly Arg Gly Ser Ala Gly Gly
            20              25              30

Asn Ala His Ser Pro Leu Gly Val Pro Gly Gly Gly Leu Pro Glu His
        35              40              45

Thr Phe Asn Leu Lys Met Phe Leu Glu Asn Val Lys Val Asp Phe Leu
    50              55              60

Arg Ser Leu Asn Leu Ser Gly Val Pro Ser Gln Asp Lys Thr Arg Val
65              70              75              80

Glu Pro Pro Gln Tyr Met Ile Asp Leu Tyr Asn Arg Tyr Thr Ser Asp
            85              90              95

Lys Ser Thr Thr Pro Ala Ser Asn Ile Val Arg Ser Phe Ser Met Glu
            100             105             110

Asp Ala Ile Ser Ile Thr Ala Thr Glu Asp Phe Pro Phe Gln Lys His
        115             120             125

Ile Leu Leu Phe Asn Ile Ser Ile Pro Arg His Glu Gln Ile Thr Arg
    130             135             140

Ala Glu Leu Arg Leu Tyr Val Ser Cys Gln Asn His Val Asp Pro Ser
145             150             155             160
```

-continued

```
His Asp Leu Lys Gly Ser Val Val Ile Tyr Asp Val Leu Asp Gly Thr
            165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
            245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
            275                 280                 285

Ser Thr Glu Ala Gly Glu Ser Ser His Glu Glu Asp Thr Asp Gly His
        290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
            325                 330                 335

Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys Pro Arg Ile Val Gln Thr Leu Val His Leu Lys Phe Pro Thr Lys
        370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
            405                 410                 415

Gly Met Ser Val Ala Glu Cys Gly Cys Arg
            420                 425
```

```
<210> SEQ ID NO 20
<211> LENGTH: 426
<212> TYPE: PRT
<213> ORGANISM: Artificial Sequence
<220> FEATURE:
<223> OTHER INFORMATION: Synthetic construct

<400> SEQUENCE: 20
```

```
Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
            35                  40                  45

Thr Phe Asn Leu Lys Met Phe Leu Glu Asn Val Lys Val Asp Phe Leu
        50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
            85                  90                  95
```

-continued

```
Lys Ser Thr Thr Pro Ala Ser Asn Ile Val Arg Ser Phe Ser Met Glu
        100                 105                 110

Asp Ala Ile Ser Ile Thr Ala Thr Glu Asp Phe Pro Phe Gln Lys His
        115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
            340                 345                 350

Cys Lys Gly Gly Cys Phe Trp Pro Leu Ala Asp Asp Val Thr Pro Thr
            355                 360                 365

Lys His Ala Ile Val Gln Thr Leu Val His Leu Lys Tyr Pro Thr Lys
    370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg
                420                 425
```

```
<210> SEQ ID NO 21
<211> LENGTH: 426
<212> TYPE: PRT
<213> ORGANISM: Artificial Sequence
<220> FEATURE:
<223> OTHER INFORMATION: Synthetic construct

<400> SEQUENCE: 21

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
        20                  25                  30
```

-continued

```
Asn Ala His Ser Pro Leu Gly Val Pro Gly Gly Gly Leu Pro Glu His
        35              40              45

Thr Phe Asn Leu Lys Met Phe Leu Glu Asn Val Lys Val Asp Phe Leu
        50              55              60

Arg Ser Leu Asn Leu Ser Gly Val Pro Ser Gln Asp Lys Thr Arg Val
65              70              75              80

Glu Pro Pro Gln Tyr Met Ile Asp Leu Tyr Asn Arg Tyr Thr Ser Asp
                85              90              95

Lys Ser Thr Thr Pro Ala Ser Asn Ile Val Arg Ser Phe Ser Met Glu
            100             105             110

Asp Ala Ile Ser Ile Thr Ala Thr Glu Asp Phe Pro Phe Gln Lys His
            115             120             125

Ile Leu Leu Phe Asn Ile Ser Ile Pro Arg His Glu Gln Ile Thr Arg
        130             135             140

Ala Glu Leu Arg Leu Tyr Val Ser Cys Gln Asn His Val Asp Pro Ser
145             150             155             160

His Asp Leu Lys Gly Ser Val Val Ile Tyr Asp Val Leu Asp Gly Thr
            165             170             175

Asp Ala Trp Asp Ser Ala Thr Glu Thr Lys Thr Phe Leu Val Ser Gln
            180             185             190

Asp Ile Gln Asp Glu Gly Trp Glu Thr Leu Glu Val Ser Ser Ala Val
            195             200             205

Lys Arg Trp Val Arg Ser Asp Ser Thr Lys Ser Lys Asn Lys Leu Glu
        210             215             220

Val Thr Val Glu Ser His Arg Lys Gly Cys Asp Thr Leu Asp Ile Ser
225             230             235             240

Val Pro Pro Gly Ser Arg Asn Leu Pro Phe Phe Val Val Phe Ser Asn
            245             250             255

Asp His Ser Ser Gly Thr Lys Glu Thr Arg Leu Glu Leu Arg Glu Met
            260             265             270

Ile Ser His Glu Gln Glu Ser Val Leu Lys Lys Leu Ser Lys Asp Gly
            275             280             285

Ser Thr Glu Ala Gly Glu Ser Ser His Glu Glu Asp Thr Asp Gly His
        290             295             300

Val Ala Ala Gly Ser Thr Leu Ala Arg Arg Lys Arg Ser Ala Gly Ala
305             310             315             320

Gly Ser His Cys Gln Lys Thr Ser Leu Arg Val Asn Phe Glu Asp Ile
            325             330             335

Gly Trp Asp Ser Trp Ile Ile Ala Pro Lys Glu Tyr Glu Ala Tyr Glu
            340             345             350

Cys Lys Gly Gly Cys Phe Phe Pro Cys Ala Asp Asp Val Thr Pro Thr
            355             360             365

Lys His Cys Ile Asp Gln Thr Leu Asp His Leu Lys Phe Pro Thr Lys
        370             375             380

Val Gly Lys Ala Cys Cys Val Pro Thr Lys Leu Ser Pro Ile Ser Val
385             390             395             400

Leu Tyr Lys Asp Asp Met Gly Val Pro Thr Leu Lys Tyr His Tyr Glu
                405             410             415

Gly Met Ser Val Ala Glu Cys Gly Cys Arg
            420             425
```

<210> SEQ ID NO 22
<211> LENGTH: 426
<212> TYPE: PRT

<213> ORGANISM: Artificial Sequence
<220> FEATURE:
<223> OTHER INFORMATION: Synthetic construct

<400> SEQUENCE: 22

```
Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
                20                  25                  30

Asn Ala His Ser Pro Leu Gly Val Pro Gly Gly Gly Leu Pro Glu His
            35                  40                  45

Thr Phe Asn Leu Lys Met Phe Leu Glu Asn Val Lys Val Asp Phe Leu
        50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
        130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
            275                 280                 285

Ser Thr Glu Ala Gly Glu Ser Ser His Glu Glu Asp Thr Asp Gly His
        290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys His Ala Ile Val Gln Thr Leu Val His Leu Lys Cys Gly Gly Lys
        370                 375                 380

Val Gly Lys Ala Cys Cys Val Pro Thr Lys Leu Ser Pro Ile Ser Val
```

-continued

```
385             390             395             400

Leu Tyr Lys Asp Asp Met Gly Val Pro Thr Leu Lys Tyr His Tyr Glu
                405             410             415

Gly Met Ser Val Ala Glu Cys Gly Cys Arg
                420             425
```

```
<210> SEQ ID NO 23
<211> LENGTH: 426
<212> TYPE: PRT
<213> ORGANISM: Artificial Sequence
<220> FEATURE:
<223> OTHER INFORMATION: Synthetic construct

<400> SEQUENCE: 23

Met Ala Trp Val Trp Thr Leu Leu Phe Leu Met Ala Ala Ala Gln Ser
1               5               10              15

Ile Gln Ala Lys Pro Leu Gln Ser Trp Gly Arg Gly Ser Ala Gly Gly
                20              25              30

Asn Ala His Ser Pro Leu Gly Val Pro Gly Gly Gly Leu Pro Glu His
        35              40              45

Thr Phe Asn Leu Lys Met Phe Leu Glu Asn Val Lys Val Asp Phe Leu
        50              55              60

Arg Ser Leu Asn Leu Ser Gly Val Pro Ser Gln Asp Lys Thr Arg Val
65              70              75              80

Glu Pro Pro Gln Tyr Met Ile Asp Leu Tyr Asn Arg Tyr Thr Ser Asp
                85              90              95

Lys Ser Thr Thr Pro Ala Ser Asn Ile Val Arg Ser Phe Ser Met Glu
                100             105             110

Asp Ala Ile Ser Ile Thr Ala Thr Glu Asp Phe Pro Phe Gln Lys His
        115             120             125

Ile Leu Leu Phe Asn Ile Ser Ile Pro Arg His Glu Gln Ile Thr Arg
        130             135             140

Ala Glu Leu Arg Leu Tyr Val Ser Cys Gln Asn His Val Asp Pro Ser
145             150             155             160

His Asp Leu Lys Gly Ser Val Val Ile Tyr Asp Val Leu Asp Gly Thr
                165             170             175

Asp Ala Trp Asp Ser Ala Thr Glu Thr Lys Thr Phe Leu Val Ser Gln
                180             185             190

Asp Ile Gln Asp Glu Gly Trp Glu Thr Leu Glu Val Ser Ser Ala Val
        195             200             205

Lys Arg Trp Val Arg Ser Asp Ser Thr Lys Ser Lys Asn Lys Leu Glu
        210             215             220

Val Thr Val Glu Ser His Arg Lys Gly Cys Asp Thr Leu Asp Ile Ser
225             230             235             240

Val Pro Pro Gly Ser Arg Asn Leu Pro Phe Phe Val Val Phe Ser Asn
                245             250             255

Asp His Ser Ser Gly Thr Lys Glu Thr Arg Leu Glu Leu Arg Glu Met
        260             265             270

Ile Ser His Glu Gln Glu Ser Val Leu Lys Lys Leu Ser Lys Asp Gly
        275             280             285

Ser Thr Glu Ala Gly Glu Ser Ser His Glu Glu Asp Thr Asp Gly His
        290             295             300

Val Ala Ala Gly Ser Thr Leu Ala Arg Arg Lys Arg Ser Ala Gly Ala
305             310             315             320

Gly Ser His Cys Gln Lys Thr Ser Leu Arg Val Asn Phe Glu Asp Ile
```

-continued

```
                325               330               335

Gly Trp Asp Ser Trp Ile Ile Ala Pro Lys Glu Tyr Glu Ala Tyr Glu
        340               345               350

Cys Lys Gly Gly Cys Phe Phe Pro Cys Ala Asp Asp Val Thr Pro Thr
        355               360               365

Lys His Cys Ile Asp Gln Thr Leu Asp His Leu Lys Phe Pro Thr Lys
    370               375               380

Val Gly Lys Asp Cys Cys Val Pro Thr Lys Ile Ser Pro Ile Ser Val
385               390               395               400

Leu Trp Lys Asp Asp Met Gly Val Pro Thr Leu Lys Tyr His Tyr Glu
                405               410               415

Gly Met Ser Val Ala Glu Cys Gly Cys Arg
                420               425

<210> SEQ ID NO 24
<211> LENGTH: 426
<212> TYPE: PRT
<213> ORGANISM: Artificial Sequence
<220> FEATURE:
<223> OTHER INFORMATION: Synthetic construct

<400> SEQUENCE: 24

Met Ala Trp Val Trp Thr Leu Leu Phe Leu Met Ala Ala Ala Gln Ser
1               5                 10                15

Ile Gln Ala Lys Pro Leu Gln Ser Trp Gly Arg Gly Ser Ala Gly Gly
        20                25                30

Asn Ala His Ser Pro Leu Gly Val Pro Gly Gly Gly Leu Pro Glu His
        35                40                45

Thr Phe Asn Leu Lys Met Phe Leu Glu Asn Val Lys Val Asp Phe Leu
    50                55                60

Arg Ser Leu Asn Leu Ser Gly Val Pro Ser Gln Asp Lys Thr Arg Val
65                70                75                80

Glu Pro Pro Gln Tyr Met Ile Asp Leu Tyr Asn Arg Tyr Thr Ser Asp
                85                90                95

Lys Ser Thr Thr Pro Ala Ser Asn Ile Val Arg Ser Phe Ser Met Glu
        100               105               110

Asp Ala Ile Ser Ile Thr Ala Thr Glu Asp Phe Pro Phe Gln Lys His
        115               120               125

Ile Leu Leu Phe Asn Ile Ser Ile Pro Arg His Glu Gln Ile Thr Arg
        130               135               140

Ala Glu Leu Arg Leu Tyr Val Ser Cys Gln Asn His Val Asp Pro Ser
145               150               155               160

His Asp Leu Lys Gly Ser Val Val Ile Tyr Asp Val Leu Asp Gly Thr
                165               170               175

Asp Ala Trp Asp Ser Ala Thr Glu Thr Lys Thr Phe Leu Val Ser Gln
        180               185               190

Asp Ile Gln Asp Glu Gly Trp Glu Thr Leu Glu Val Ser Ser Ala Val
        195               200               205

Lys Arg Trp Val Arg Ser Asp Ser Thr Lys Ser Lys Asn Lys Leu Glu
        210               215               220

Val Thr Val Glu Ser His Arg Lys Gly Cys Asp Thr Leu Asp Ile Ser
225               230               235               240

Val Pro Pro Gly Ser Arg Asn Leu Pro Phe Phe Val Val Phe Ser Asn
                245               250               255

Asp His Ser Ser Gly Thr Lys Glu Thr Arg Leu Glu Leu Arg Glu Met
```

-continued

```
                 260                 265                 270
Ile Ser His Glu Gln Glu Ser Val Leu Lys Lys Leu Ser Lys Asp Gly
            275                 280                 285

Ser Thr Glu Ala Gly Glu Ser Ser His Glu Glu Asp Thr Asp Gly His
        290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
                325                 330                 335

Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys His Ala Ile Val Gln Thr Leu Val His Leu Lys Cys Gly Gly Lys
        370                 375                 380

Val Gly Lys Ala Cys Cys Ala Pro Thr Pro Leu Ser Pro Ile Ser Val
385                 390                 395                 400

Leu Trp Lys Asp Asp Met Gly Val Pro Thr Leu Lys Tyr His Tyr Glu
                405                 410                 415

Gly Met Ser Val Ala Glu Cys Gly Cys Arg
            420                 425

<210> SEQ ID NO 25
<211> LENGTH: 426
<212> TYPE: PRT
<213> ORGANISM: Artificial Sequence
<220> FEATURE:
<223> OTHER INFORMATION: Synthetic construct

<400> SEQUENCE: 25

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
        50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
            115                 120                 125

Ile Leu Leu Phe Asn Ile Ser Ile Pro Arg His Glu Gln Ile Thr Arg
        130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
```

```
            195              200              205
    Lys Arg Trp Val Arg Ser Asp Ser Thr Lys Ser Lys Asn Lys Leu Glu
        210              215              220

Val Thr Val Glu Ser His Arg Lys Gly Cys Asp Thr Leu Asp Ile Ser
    225              230              235              240

Val Pro Pro Gly Ser Arg Asn Leu Pro Phe Phe Val Phe Ser Asn
                     245              250              255

Asp His Ser Ser Gly Thr Lys Glu Thr Arg Leu Glu Leu Arg Glu Met
                 260              265              270

Ile Ser His Glu Gln Glu Ser Val Leu Lys Lys Leu Ser Lys Asp Gly
                 275              280              285

Ser Thr Glu Ala Gly Glu Ser Ser His Glu Glu Asp Thr Asp Gly His
                 290              295              300

Val Ala Ala Gly Ser Thr Leu Ala Arg Arg Lys Arg Ser Ala Gly Ala
    305              310              315              320

Gly Ser His Cys Gln Lys Thr Ser Leu Arg Val Asn Phe Glu Asp Ile
                     325              330              335

Gly Trp Asp Ser Trp Ile Ile Ala Pro Lys Glu Tyr Glu Ala Tyr Glu
                 340              345              350

Cys Lys Gly Gly Cys Phe Phe Pro Leu Ala Ala Asp Val Thr Pro Thr
                 355              360              365

Lys His Ala Ile Val Gln Thr Leu Val His Leu Lys Phe Pro Thr Lys
        370              375              380

Val Gly Lys Ala Cys Cys Val Pro Thr Lys Leu Ser Pro Ile Ser Val
    385              390              395              400

Leu Tyr Lys Asp Asp Met Gly Val Pro Thr Leu Lys Tyr His Tyr Glu
                     405              410              415

Gly Met Ser Val Ala Glu Cys Gly Cys Arg
                 420              425
```

<210> SEQ ID NO 26
<211> LENGTH: 426
<212> TYPE: PRT
<213> ORGANISM: Artificial Sequence
<220> FEATURE:
<223> OTHER INFORMATION: Synthetic construct

<400> SEQUENCE: 26

```
    Met Ala Trp Val Trp Thr Leu Leu Phe Leu Met Ala Ala Ala Gln Ser
    1               5               10              15

Ile Gln Ala Lys Pro Leu Gln Ser Trp Gly Arg Gly Ser Ala Gly Gly
                20              25              30

Asn Ala His Ser Pro Leu Gly Val Pro Gly Gly Gly Leu Pro Glu His
            35              40              45

Thr Phe Asn Leu Lys Met Phe Leu Glu Asn Val Lys Val Asp Phe Leu
        50              55              60

Arg Ser Leu Asn Leu Ser Gly Val Pro Ser Gln Asp Lys Thr Arg Val
    65              70              75              80

Glu Pro Pro Gln Tyr Met Ile Asp Leu Tyr Asn Arg Tyr Thr Ser Asp
                    85              90              95

Lys Ser Thr Thr Pro Ala Ser Asn Ile Val Arg Ser Phe Ser Met Glu
                100             105             110

Asp Ala Ile Ser Ile Thr Ala Thr Glu Asp Phe Pro Phe Gln Lys His
            115             120             125

Ile Leu Leu Phe Asn Ile Ser Ile Pro Arg His Glu Gln Ile Thr Arg
```

-continued

```
        130              135              140

Ala Glu Leu Arg Leu Tyr Val Ser Cys Gln Asn His Val Asp Pro Ser
145              150              155              160

His Asp Leu Lys Gly Ser Val Val Ile Tyr Asp Val Leu Asp Gly Thr
            165              170              175

Asp Ala Trp Asp Ser Ala Thr Glu Thr Lys Thr Phe Leu Val Ser Gln
            180              185              190

Asp Ile Gln Asp Glu Gly Trp Glu Thr Leu Glu Val Ser Ser Ala Val
            195              200              205

Lys Arg Trp Val Arg Ser Asp Ser Thr Lys Ser Lys Asn Lys Leu Glu
        210              215              220

Val Thr Val Glu Ser His Arg Lys Gly Cys Asp Thr Leu Asp Ile Ser
225              230              235              240

Val Pro Pro Gly Ser Arg Asn Leu Pro Phe Phe Val Val Phe Ser Asn
            245              250              255

Asp His Ser Ser Gly Thr Lys Glu Thr Arg Leu Glu Leu Arg Glu Met
            260              265              270

Ile Ser His Glu Gln Glu Ser Val Leu Lys Lys Leu Ser Lys Asp Gly
            275              280              285

Ser Thr Glu Ala Gly Glu Ser Ser His Glu Glu Asp Thr Asp Gly His
        290              295              300

Val Ala Ala Gly Ser Thr Leu Ala Arg Arg Lys Arg Ser Ala Gly Ala
305              310              315              320

Gly Ser His Cys Gln Lys Thr Ser Leu Arg Val Asn Phe Glu Asp Ile
            325              330              335

Gly Trp Asp Ser Trp Ile Ile Ala Pro Lys Glu Tyr Glu Ala Tyr Glu
            340              345              350

Cys Lys Gly Gly Cys Phe Phe Pro Leu Ala Asp Asp Val Thr Pro Thr
            355              360              365

Lys His Ala Ile Val Gln Thr Leu Val His Leu Lys Phe Pro Thr Lys
        370              375              380

Val Gly Lys Ala Cys Cys Val Pro Thr Lys Leu Ser Pro Ile Ser Val
385              390              395              400

Leu Tyr Lys Asp Ala Met Gly Val Pro Thr Leu Lys Tyr His Tyr Glu
            405              410              415

Gly Met Ser Val Ala Glu Cys Gly Cys Arg
            420              425
```

<210> SEQ ID NO 27
<211> LENGTH: 426
<212> TYPE: PRT
<213> ORGANISM: Artificial Sequence
<220> FEATURE:
<223> OTHER INFORMATION: Synthetic construct

<400> SEQUENCE: 27

```
Met Ala Trp Val Trp Thr Leu Leu Phe Leu Met Ala Ala Ala Gln Ser
1               5               10               15

Ile Gln Ala Lys Pro Leu Gln Ser Trp Gly Arg Gly Ser Ala Gly Gly
            20               25               30

Asn Ala His Ser Pro Leu Gly Val Pro Gly Gly Gly Leu Pro Glu His
            35               40               45

Thr Phe Asn Leu Lys Met Phe Leu Glu Asn Val Lys Val Asp Phe Leu
        50               55               60

Arg Ser Leu Asn Leu Ser Gly Val Pro Ser Gln Asp Lys Thr Arg Val
```

-continued

```
            65                    70                    75                    80

Glu Pro Pro Gln Tyr Met Ile Asp Leu Tyr Asn Arg Tyr Thr Ser Asp
                    85                    90                    95

Lys Ser Thr Thr Pro Ala Ser Asn Ile Val Arg Ser Phe Ser Met Glu
                    100                   105                   110

Asp Ala Ile Ser Ile Thr Ala Thr Glu Asp Phe Pro Phe Gln Lys His
                    115                   120                   125

Ile Leu Leu Phe Asn Ile Ser Ile Pro Arg His Glu Gln Ile Thr Arg
                    130                   135                   140

Ala Glu Leu Arg Leu Tyr Val Ser Cys Gln Asn His Val Asp Pro Ser
145                   150                   155                   160

His Asp Leu Lys Gly Ser Val Val Ile Tyr Asp Val Leu Asp Gly Thr
                    165                   170                   175

Asp Ala Trp Asp Ser Ala Thr Glu Thr Lys Thr Phe Leu Val Ser Gln
                    180                   185                   190

Asp Ile Gln Asp Glu Gly Trp Glu Thr Leu Glu Val Ser Ser Ala Val
                    195                   200                   205

Lys Arg Trp Val Arg Ser Asp Ser Thr Lys Ser Lys Asn Lys Leu Glu
                    210                   215                   220

Val Thr Val Glu Ser His Arg Lys Gly Cys Asp Thr Leu Asp Ile Ser
225                   230                   235                   240

Val Pro Pro Gly Ser Arg Asn Leu Pro Phe Phe Val Val Phe Ser Asn
                    245                   250                   255

Asp His Ser Ser Gly Thr Lys Glu Thr Arg Leu Glu Leu Arg Glu Met
                    260                   265                   270

Ile Ser His Glu Gln Glu Ser Val Leu Lys Lys Leu Ser Lys Asp Gly
                    275                   280                   285

Ser Thr Glu Ala Gly Glu Ser Ser His Glu Glu Asp Thr Asp Gly His
                    290                   295                   300

Val Ala Ala Gly Ser Thr Leu Ala Arg Arg Lys Arg Ser Ala Gly Ala
305                   310                   315                   320

Gly Ser His Cys Gln Lys Thr Ser Leu Arg Val Asn Phe Glu Asp Ile
                    325                   330                   335

Gly Trp Asp Ser Trp Ile Ile Ala Pro Lys Glu Tyr Glu Ala Tyr Glu
                    340                   345                   350

Cys Lys Gly Gly Cys Phe Phe Pro Leu Ala Glu Asp Val Thr Pro Thr
                    355                   360                   365

Lys His Ala Ile Val Gln Thr Leu Val His Leu Lys Phe Pro Thr Lys
                    370                   375                   380

Val Gly Lys Ala Cys Cys Val Pro Thr Lys Leu Ser Pro Ile Ser Val
385                   390                   395                   400

Leu Tyr Lys Asp Asp Met Gly Val Pro Thr Leu Lys Tyr His Tyr Glu
                    405                   410                   415

Gly Met Ser Val Ala Glu Cys Gly Cys Arg
                    420                   425
```

```
<210> SEQ ID NO 28
<211> LENGTH: 426
<212> TYPE: PRT
<213> ORGANISM: Artificial Sequence
<220> FEATURE:
<223> OTHER INFORMATION: Synthetic construct

<400> SEQUENCE: 28

Met Ala Trp Val Trp Thr Leu Leu Phe Leu Met Ala Ala Ala Gln Ser
```

-continued

```
1               5               10              15

Ile Gln Ala Lys Pro Leu Gln Ser Trp Gly Arg Gly Ser Ala Gly Gly
              20              25              30

Asn Ala His Ser Pro Leu Gly Val Pro Gly Gly Gly Leu Pro Glu His
              35              40              45

Thr Phe Asn Leu Lys Met Phe Leu Glu Asn Val Lys Val Asp Phe Leu
      50              55              60

Arg Ser Leu Asn Leu Ser Gly Val Pro Ser Gln Asp Lys Thr Arg Val
65              70              75              80

Glu Pro Pro Gln Tyr Met Ile Asp Leu Tyr Asn Arg Tyr Thr Ser Asp
              85              90              95

Lys Ser Thr Thr Pro Ala Ser Asn Ile Val Arg Ser Phe Ser Met Glu
              100             105             110

Asp Ala Ile Ser Ile Thr Ala Thr Glu Asp Phe Pro Phe Gln Lys His
              115             120             125

Ile Leu Leu Phe Asn Ile Ser Ile Pro Arg His Glu Gln Ile Thr Arg
      130             135             140

Ala Glu Leu Arg Leu Tyr Val Ser Cys Gln Asn His Val Asp Pro Ser
145             150             155             160

His Asp Leu Lys Gly Ser Val Val Ile Tyr Asp Val Leu Asp Gly Thr
              165             170             175

Asp Ala Trp Asp Ser Ala Thr Glu Thr Lys Thr Phe Leu Val Ser Gln
              180             185             190

Asp Ile Gln Asp Glu Gly Trp Glu Thr Leu Glu Val Ser Ser Ala Val
              195             200             205

Lys Arg Trp Val Arg Ser Asp Ser Thr Lys Ser Lys Asn Lys Leu Glu
      210             215             220

Val Thr Val Glu Ser His Arg Lys Gly Cys Asp Thr Leu Asp Ile Ser
225             230             235             240

Val Pro Pro Gly Ser Arg Asn Leu Pro Phe Phe Val Val Phe Ser Asn
              245             250             255

Asp His Ser Ser Gly Thr Lys Glu Thr Arg Leu Glu Leu Arg Glu Met
              260             265             270

Ile Ser His Glu Gln Glu Ser Val Leu Lys Lys Leu Ser Lys Asp Gly
      275             280             285

Ser Thr Glu Ala Gly Glu Ser Ser His Glu Glu Asp Thr Asp Gly His
      290             295             300

Val Ala Ala Gly Ser Thr Leu Ala Arg Arg Lys Arg Ser Ala Gly Ala
305             310             315             320

Gly Ser His Cys Gln Lys Thr Ser Leu Arg Val Asn Phe Glu Asp Ile
              325             330             335

Gly Trp Asp Ser Trp Ile Ile Ala Pro Lys Glu Tyr Glu Ala Tyr Glu
              340             345             350

Cys Lys Gly Gly Cys Phe Phe Pro Leu Ala Ala Asp Val Thr Pro Thr
              355             360             365

Lys His Ala Ile Val Gln Thr Leu Val His Leu Lys Phe Pro Thr Lys
      370             375             380

Val Gly Lys Ala Cys Cys Val Pro Thr Lys Leu Ser Pro Ile Ser Val
385             390             395             400

Leu Tyr Lys Asp Ala Met Gly Val Pro Thr Leu Lys Tyr His Tyr Glu
              405             410             415

Gly Met Ser Val Ala Glu Cys Gly Cys Arg
              420             425
```

-continued

```
<210> SEQ ID NO 29
<211> LENGTH: 24
<212> TYPE: PRT
<213> ORGANISM: Artificial Sequence
<220> FEATURE:
<223> OTHER INFORMATION: Synthetic construct

<400> SEQUENCE: 29

Phe Phe Pro Leu Ala Asp Asp Val Thr Pro Thr Lys His Ala Ile Val
1               5                   10                  15

Gln Thr Leu Val His Leu Lys Phe
            20

<210> SEQ ID NO 30
<211> LENGTH: 243
<212> TYPE: PRT
<213> ORGANISM: Artificial Sequence
<220> FEATURE:
<223> OTHER INFORMATION: Synthetic construct

<400> SEQUENCE: 30

Met Ala Trp Val Trp Thr Leu Leu Phe Leu Met Ala Ala Ala Gln Ser
1               5                   10                  15

Ile Gln Ala His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
            35                  40                  45

Ile Ser Arg Thr Pro Glu Val Thr Cys Val Val Val Asp Val Ser His
        50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
                100                 105                 110

Lys Glu Tyr Lys Cys Lys Val Ser Asn Lys Ala Leu Pro Ala Pro Ile
            115                 120                 125

Glu Lys Thr Ile Ser Lys Ala Lys Gly Gln Pro Arg Glu Pro Gln Val
        130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
                180                 185                 190

Val Leu Asp Ser Asp Gly Ser Phe Phe Leu Tyr Ser Lys Leu Thr Val
            195                 200                 205

Asp Lys Ser Arg Trp Gln Gln Gly Asn Val Phe Ser Cys Ser Val Met
        210                 215                 220

His Glu Ala Leu His Asn His Tyr Thr Gln Lys Ser Leu Ser Leu Ser
225                 230                 235                 240

Pro Gly Lys

<210> SEQ ID NO 31
<211> LENGTH: 15
<212> TYPE: PRT
<213> ORGANISM: Artificial Sequence
```

```
<220> FEATURE:
<223> OTHER INFORMATION: Synthetic construct

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 368
<212> TYPE: PRT
<213> ORGANISM: Artificial Sequence
<220> FEATURE:
<223> OTHER INFORMATION: Synthetic construct

<400> SEQUENCE: 32

Met Ala Trp Val Trp Thr Leu Leu Phe Leu Met Ala Ala Ala Gln Ser
1               5                   10                  15

Ile Gln Ala His Thr Cys Pro Pro Cys Pro Ala Pro Glu Leu Leu Gly
                20                  25                  30

Gly Pro Ser Val Phe Leu Phe Pro Pro Lys Pro Lys Asp Thr Leu Met
            35                  40                  45

Ile Ser Arg Thr Pro Glu Val Thr Cys Val Val Val Asp Val Ser His
        50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
                100                 105                 110

Lys Glu Tyr Lys Cys Lys Val Ser Asn Lys Ala Leu Pro Ala Pro Ile
            115                 120                 125

Glu Lys Thr Ile Ser Lys Ala Lys Gly Gln Pro Arg Glu Pro Gln Val
        130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
                180                 185                 190

Val Leu Asp Ser Asp Gly Ser Phe Phe Leu Tyr Ser Lys Leu Thr Val
            195                 200                 205

Asp Lys Ser Arg Trp Gln Gln Gly Asn Val Phe Ser Cys Ser Val Met
        210                 215                 220

His Glu Ala Leu His Asn His Tyr Thr Gln Lys Ser Leu Ser Leu Ser
225                 230                 235                 240

Pro Gly Lys Gly Gly Gly Gly Ser Gly Gly Gly Gly Ser Gly Gly Gly
                245                 250                 255

Gly Ser Ser Ala Gly Ala Gly Ser His Cys Gln Lys Thr Ser Leu Arg
            260                 265                 270

Val Asn Phe Glu Asp Ile Gly Trp Asp Ser Trp Ile Ile Ala Pro Lys
            275                 280                 285

Glu Tyr Glu Ala Tyr Glu Cys Lys Gly Gly Cys Phe Phe Pro Leu Ala
        290                 295                 300

Asp Asp Val Thr Pro Thr Lys His Ala Ile Val Gln Thr Leu Val His
305                 310                 315                 320

Leu Lys Phe Pro Thr Lys Val Gly Lys Ala Cys Cys Val Pro Thr Lys
```

-continued

```
                    325                 330                 335

Leu Ser Pro Ile Ser Val Leu Tyr Lys Asp Asp Met Gly Val Pro Thr
            340                 345                 350

Leu Lys Tyr His Tyr Glu Gly Met Ser Val Ala Glu Cys Gly Cys Arg
        355                 360                 365

<210> SEQ ID NO 33
<211> LENGTH: 665
<212> TYPE: PRT
<213> ORGANISM: Artificial Sequence
<220> FEATURE:
<223> OTHER INFORMATION: Synthetic construct

<400> SEQUENCE: 33

Met Ala Trp Val Trp Thr Leu Leu Phe Leu Met Ala Ala Ala Gln Ser
1               5                   10                  15

Ile Gln Ala Lys Pro Leu Gln Ser Trp Gly Arg Gly Ser Ala Gly Gly
            20                  25                  30

Asn Ala His Ser Pro Leu Gly Val Pro Gly Gly Gly Leu Pro Glu His
        35                  40                  45

Thr Phe Asn Leu Lys Met Phe Leu Glu Asn Val Lys Val Asp Phe Leu
    50                  55                  60

Arg Ser Leu Asn Leu Ser Gly Val Pro Ser Gln Asp Lys Thr Arg Val
65                  70                  75                  80

Glu Pro Pro Gln Tyr Met Ile Asp Leu Tyr Asn Arg Tyr Thr Ser Asp
                85                  90                  95

Lys Ser Thr Thr Pro Ala Ser Asn Ile Val Arg Ser Phe Ser Met Glu
            100                 105                 110

Asp Ala Ile Ser Ile Thr Ala Thr Glu Asp Phe Pro Phe Gln Lys His
        115                 120                 125

Ile Leu Leu Phe Asn Ile Ser Ile Pro Arg His Glu Gln Ile Thr Arg
    130                 135                 140

Ala Glu Leu Arg Leu Tyr Val Ser Cys Gln Asn His Val Asp Pro Ser
145                 150                 155                 160

His Asp Leu Lys Gly Ser Val Val Ile Tyr Asp Val Leu Asp Gly Thr
                165                 170                 175

Asp Ala Trp Asp Ser Ala Thr Glu Thr Lys Thr Phe Leu Val Ser Gln
            180                 185                 190

Asp Ile Gln Asp Glu Gly Trp Glu Thr Leu Glu Val Ser Ser Ala Val
            195                 200                 205

Lys Arg Trp Val Arg Ser Asp Ser Thr Lys Ser Lys Asn Lys Leu Glu
        210                 215                 220

Val Thr Val Glu Ser His Arg Lys Gly Cys Asp Thr Leu Asp Ile Ser
225                 230                 235                 240

Val Pro Pro Gly Ser Arg Asn Leu Pro Phe Phe Val Val Phe Ser Asn
                245                 250                 255

Asp His Ser Ser Gly Thr Lys Glu Thr Arg Leu Glu Leu Arg Glu Met
            260                 265                 270

Ile Ser His Glu Gln Glu Ser Val Leu Lys Lys Leu Ser Lys Asp Gly
        275                 280                 285

Ser Thr Glu Ala Gly Glu Ser Ser His Glu Glu Asp Thr Asp Gly His
    290                 295                 300

Val Ala Ala Gly Ser Thr Leu Ala Arg Arg Lys Arg Ser Ala Gly Ala
305                 310                 315                 320

Gly Ser His Cys Gln Lys Thr Ser Leu Arg Val Asn Phe Glu Asp Ile
```

-continued

```
                  325                 330                 335
Gly Trp Asp Ser Trp Ile Ile Ala Pro Lys Glu Tyr Glu Ala Tyr Glu
            340                 345                 350

Cys Lys Gly Gly Cys Phe Phe Pro Leu Ala Asp Asp Val Thr Pro Thr
            355                 360                 365

Lys His Ala Ile Val Gln Thr Leu Val His Leu Lys Phe Pro Thr Lys
            370                 375                 380

Val Gly Lys Ala Cys Cys Val Pro Thr Lys Leu Ser Pro Ile Ser Val
385                 390                 395                 400

Leu Tyr Lys Asp Asp Met Gly Val Pro Thr Leu Lys Tyr His Tyr Glu
                405                 410                 415

Gly Met Ser Val Ala Glu Cys Gly Cys Arg Gly Gly Gly Ser Gly
                420                 425                 430

Gly Gly Gly Ser Gly Gly Gly Ser His Thr Cys Pro Pro Cys Pro
            435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
                500                 505                 510

Gln Tyr Asn Ser Thr Tyr Arg Val Val Ser Val Leu Thr Val Leu His
            515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Asp Glu Leu
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
            595                 600                 605

Tyr Lys Thr Thr Pro Pro Val Leu Asp Ser Asp Gly Ser Phe Phe Leu
    610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Lys
            660                 665
```

<210> SEQ ID NO 34
<211> LENGTH: 20
<212> TYPE: PRT
<213> ORGANISM: Artificial Sequence
<220> FEATURE:
<223> OTHER INFORMATION: Synthetic construct -continued

```
<400> SEQUENCE: 34

Lys Val Gly Lys Ala Cys Cys Val Pro Thr Lys Leu Ser Pro Ile Ser
1               5                   10                  15

Val Leu Tyr Lys
            20
```